United States Patent
Zhang et al.

(10) Patent No.: US 11,883,501 B2
(45) Date of Patent: *Jan. 30, 2024

(54) SELECTIVE CXCR4 BINDING PEPTIDE CONJUGATE AND METHODS FOR MAKING AND USING THE SAME

(71) Applicant: Mainline Biosciences (Shanghai) Co., Ltd., Shanghai (CN)

(72) Inventors: Junge Zhang, Malvern, PA (US); Liang Zeng Yan, Camel, IN (US)

(73) Assignee: Mainline Biosciences (Shanghai) Co., Ltd., Shanghai (CN)

( * ) Notice: Subject to any disclaimer, the term of this patent is extended or adjusted under 35 U.S.C. 154(b) by 154 days.

This patent is subject to a terminal disclaimer.

(21) Appl. No.: 17/479,920

(22) Filed: Sep. 20, 2021

(65) Prior Publication Data

US 2022/0062433 A1   Mar. 3, 2022

Related U.S. Application Data

(63) Continuation of application No. 16/752,690, filed on Jan. 26, 2020, now Pat. No. 11,123,437, which is a continuation-in-part of application No. 15/898,434, filed on Feb. 17, 2018, now Pat. No. 10,639,379.

(60) Provisional application No. 62/554,354, filed on Sep. 5, 2017.

(51) Int. Cl.
*A61K 47/64* (2017.01)
*C07K 7/06* (2006.01)

(52) U.S. Cl.
CPC ............. *A61K 47/64* (2017.08); *C07K 7/06* (2013.01)

(58) Field of Classification Search
None
See application file for complete search history.

(56) References Cited

U.S. PATENT DOCUMENTS

| | | | |
|---|---|---|---|
| RE42,274 E | | 4/2011 | Kohn et al. |
| 10,639,379 B2* | | 5/2020 | Zhang ............ G01N 33/566 |
| 11,123,437 B2* | | 9/2021 | Zhang ............ C07K 7/06 |
| 2006/0004101 A1 | | 1/2006 | Okita |
| 2008/0300177 A1 | | 12/2008 | Kohn et al. |
| 2010/0130409 A1 | | 5/2010 | Kohn et al. |
| 2011/0027175 A1 | | 2/2011 | Wester et al. |
| 2011/0280827 A1 | | 11/2011 | Hu et al. |
| 2013/0079292 A1 | | 3/2013 | Amodeo et al. |
| 2014/0135381 A1 | | 5/2014 | Hadwiger et al. |
| 2015/0050351 A1 | | 2/2015 | Gonzalez |
| 2015/0218219 A1 | | 8/2015 | Gombert et al. |

FOREIGN PATENT DOCUMENTS

| | | | | |
|---|---|---|---|---|
| CN | 101678213 A | 3/2010 | | |
| CN | 102626522 A | 8/2012 | | |
| CN | 102869675 A | 1/2013 | | |
| WO | WO 2007/096662 A2 | 8/2007 | | |
| WO | WO 2008/150689 A1 | 12/2008 | | |
| WO | WO 2015/185162 A1 | 12/2015 | | |
| WO | WO-2015185162 A1 * | 12/2015 | ............. | A61K 51/08 |
| WO | WO 2018/048806 A1 | 3/2018 | | |
| WO | WO 2019/050564 A1 | 3/2019 | | |

OTHER PUBLICATIONS

1st Office Action of Chinese Patent Application No. 2017800542505, dated Aug. 31, 2022.
2nd Office Action of Chinese Patent Application No. 2017800542505, dated Feb. 7, 2023.
3rd Office Action of Chinese Patent Application No. 2017800542505, dated May 6, 2023.
Supplementary Partial European Search Report of EP Application No. 17 84 9397, dated Dec. 21, 2020.
Extended European Search Report of EP Application No. 17 84 9397, dated Jun. 22, 2021.
Peng et al., "Identification of LY2510924, a Novel Cyclic Peptide CXCR4 Antagonist that Exhibits Antitumor Activities in Solid Tumor and Breast Cancer Metastatic Models," Mol. Cancer Ther., 2015, vol. 14 (2), pp. 480-490.
Yasushi, Yoshikawa et al., "Molecular modelling study of cyclic pentapeptide CXCR4 antagonists: New insight into CXCR4FC131 Interactions," Bioorg. & Med. Chem. Letts., 2012, vol. 22(6), pp. 2146-2150.

(Continued)

*Primary Examiner* — Sudhakar Katakam
*Assistant Examiner* — Zachary J Miknis
(74) *Attorney, Agent, or Firm* — Don D. Cha; HDC Intellectual Property Law, LLP

(57) ABSTRACT

The present invention provides a selective CXCR4 binding peptide conjugate ("PC"), and a method for using and producing the same. In particular, the selective CXCR4 binding peptide conjugate of the invention comprises a peptide portion that selectively binds to CXCR4 and a medically useful compound, such as an imaging agent, a diagnostic agent, or a therapeutically or pharmaceutically active compound. In one particular embodiment, the selective CXCR4 binding peptide conjugate ("PC") is of the formula:

(SEQ ID NO: 1)

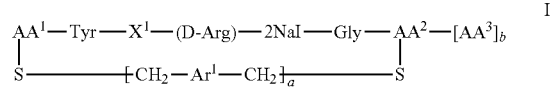

or a pharmaceutically acceptable salt thereof, wherein a, b, $AA^1$, $AA^2$, $Ar^1$, $X^1$, and $AA^3$ are those defined herein. The peptide conjugate of the invention can be used in a variety of medical applications including, but not limited to, a targeted drug delivery or imaging a patient or diagnosing a patient for a disease or a clinical condition associated with overexpression and/or upregulation of CXCR4, such as cancers, HIV infection, and immune disorders. Compositions, kits and methods are also disclosed herein for such uses.

11 Claims, No Drawings

Specification includes a Sequence Listing.

(56) References Cited

OTHER PUBLICATIONS

1st Office Action of Japanese Patent Appl. No. 2019-533297, dated Sep. 1, 2021.
2nd Office Action of Japanese Patent Appl. No. 2019-533297, dated Mar. 3, 2022.
International Search Report of PCT Patent Application No. PCT/US17/50106, dated Feb. 14, 2018.
Office Action of U.S. Appl. No. 16/431,657, dated Dec. 13, 2019.
Southern Cross, downloaded on Nov. 20, 2019 from U R L: <https://www.southerncross.co.nz/group/medical-library/rheumatoid-arthritis-causes-symptoms-treatment> (Year: 2019).
Pulmonary Fibrosis News, downloaded on Nov. 20, 2019 from URL:<https://pulmonaryfibrosisnews.com/pulmonary-fibrosis-prevention I (Year: 2019).
CDC HIV, downloaded on Nov. 20, 2019 from URL:<https://www.cdc.gov/hiv/basics/prevention.html> (Year: 2019).
Ovarian cancer WebMD, downloaded on Nov. 20, 2019 from URL:<https://www.webmd.com/ovarian-cancerlcan-i-prevent-ovarian-cancer> (Year: 2019).
Bladder cancer WebMD, downloaded on Nov. 20, 2019 from U RL:<hUps://www.webmd.com/cancer/bladder-cancer/understanding-bladder-cancer-prevention> (Year: 2019).
International Search Report of PCT Patent Application No. PCT/US2018/018530, dated Jun. 14, 2018.
1st Office Action of Chinese Patent Application No. 201880049498.7, dated Feb. 16, 2023.
Supplementary Partial European Search Report of EP Application No. 18 85 2912, dated Jun. 10, 2021.
Yan Wang et al., "Potential of CXCR4/CXCL12 Chemokine Axis in Cancer Drug Delivery," Curr. Pharmaco. Rprt, 2016, vol. 2(1), pp. 1-10.
Extended European Search Report of EP Application No. 18 85 2912, dated Sep. 27, 2021.
1st Office Action of Japanese Patent Application No. 2020-504380, dated Oct. 18, 2021.
1st Office Action of Japanese Patent Application No. 2020-504380, dated Mar. 2, 2022.
Biochem, 2010, vol. 82(6), pp. 515-523 (in Japanese).
Kowalczyk et al., "Synthesis and evaluation of disulfide bond mimetics of amylin-(1-8) as agents to treat osteoporosis," Bioorg. & Med. Chem., 2012, vol. 20, pp. 2661-2668.
1st Office Action of Korean Patent Application No. 10-2020-7000227, dated Jan. 12, 2023.
2nd Office Action of Korean Patent Application No. 10-2020-7000227, dated Jul. 6, 2023.
International Search Report of PCT Patent Application No. PCT/US20/25522, dated Aug. 3, 2020.
1st Office Action of Chinese Patent Application No. 202080094623.3, dated Jan. 5, 2023.
2nd Office Action of Chinese Patent Application No. 202080094623.3, dated May 31, 2023.
1st Office Action of U.S. Appl. No. 16/752,690, dated Nov. 25, 2020.
International Search Report of PCT Patent Appl. No. PCT/US2018/067376, dated May 9, 2019.
1st Office Action of U.S. Appl. No. 16/766,741, dated Nov. 1, 2022.
2nd Office Action of U.S. Appl. No. 16/766,741, dated Mar. 7, 2023.

\* cited by examiner

SELECTIVE CXCR4 BINDING PEPTIDE CONJUGATE AND METHODS FOR MAKING AND USING THE SAME

CROSS-REFERENCE TO RELATED APPLICATIONS

This application is continuation of U.S. patent application Ser. No. 16/752,690, filed Jan. 26, 2020, which is a continuation-in-part of U.S. patent application Ser. No. 15/898,434, filed Feb. 17, 2018, now U.S. Pat. No. 10,639,379, issued May 5, 2020, which claims the priority benefit of U.S. Provisional Application No. 62/554,354, filed Sep. 5, 2017, all of which are incorporated herein by reference in their entirety.

FIELD OF THE INVENTION

The present invention relates to a selective CXCR4 binding peptide conjugate ("PC"), and a method for using and producing the same. In particular, the selective CXCR4 binding peptide conjugate of the invention comprises a peptide portion that selectively binds to CXCR4 and a medically useful compound, such as an imaging agent, a diagnostic agent, or a therapeutically or pharmaceutically active compound.

BACKGROUND OF THE INVENTION

CXCL12 (also called stromal cell-derived factor-1 or SDF-1) and CXCR4, a chemokine and chemokine receptor pair play important roles in hematopoiesis, multiple stages of tumorigenesis, and embryonic development. For example, activation of CXCR4 by CXCL12 has shown to direct leukocyte chemotaxis in the immune system in response to inflammation and progenitor cell migration during embryologic development. Activation of CXCR4 by CXCL12 has also been shown to mediate signaling pathway that is involved in breast cancer metastasis and memory T cell migration.

CXCR4, a G-protein-coupled receptor also known as fusin or CD184 (cluster of differentiation 184), is constitutively- or over-expressed in a wide variety of human cancers, promoting local tumor cell proliferation, survival and angiogenesis. It has also been reported that CXCR4 is a co-receptor for HIV entry and infection of host cells and has been evaluated as a potential HIV therapy.

Reports have confirmed that CXCR4 is overexpressed in numerous human cancers. CXCR4 antagonism has been shown to disrupt tumor-stromal interactions, sensitize cancer cells to cytotoxic drugs, and reduce tumor growth and metastatic burden. Hence, CXCR4 is a target not only for potential therapeutic intervention of cancer treatment, but also for noninvasive monitoring of disease progression, therapeutic guidance, and other diagnostic purposes. Some have even suggested that binding and interacting with CXCR4 as a potential way of targeted drug delivery.

Thus, it is believed that compounds having a moiety that can selectively bind CXCR4 (i.e., CXCR4 selective binding conjugate) can have a wide variety uses including, but not limited to, treating a wide array of clinical conditions associated with activation or over-expression of CXCR4, diagnosing a patient, and medical imaging. Moreover, by labelling a moiety that can selectively bind to CXCR4, one can study the various mode of drug delivery, drug interaction, diagnosis, in vivo imaging of cells affected by over-expression of CXCR4, etc. It would be more useful, if such a labelled compound do not significantly alter the interaction with CXCR4.

Accordingly, there is a need for conjugates that can selectively bind to CXCR4 having a medically useful compound. In addition, there is a need for a labelled conjugate that does not significantly alter the physical properties, such as a binding constant, drug activity, its three-dimensional structure, etc.

SUMMARY OF THE INVENTION

The present invention provides a selective CXCR4 binding peptide conjugate ("PC"), and a method for using and producing the same. In particular, the selective CXCR4 binding peptide conjugate of the invention comprises a peptide portion that selectively binds to CXCR4 and a medically useful compound, such as an imaging agent, a diagnostic agent, or a therapeutically or pharmaceutically active compound. The peptidyl portion of the compounds can optionally be isotopically labelled. In this manner, one can readily trace, image, or study the compounds in vivo. The peptide or peptidyl portion is linked to the medically useful compound via a polymeric linker. The peptide conjugate of the invention can be used in a variety of medical applications including, but not limited to, a targeted drug delivery, imaging a patient, studying the medically useful compound in vivo (e.g., interaction with CXCR4, etc.), diagnosing a patient for a disease or a clinical condition associated with overexpression and/or upregulation of CXCR4, such as cancers, HIV infection, and immune disorders. Compositions, kits and methods are also disclosed herein for such uses.

In one particular aspect of the invention provides a selective CXCR4 binding peptide conjugate ("PC") of the formula:

(SEQ ID NO: 1)

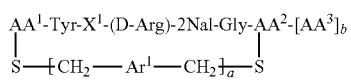

I or a pharmaceutically acceptable salt thereof,
wherein:
  a is 0 or 1;
  b is an integer from 1 to 4;
  $AA^1$ along with the sulfur atom that is attached thereto is 3-mercaptopropionic acid, optionally substituted cysteine, optionally substituted homocysteine, or optionally substituted penicillamine;
  $AA^2$ along with the sulfur atom that is attached thereto is cysteine or homocysteine;
  $Ar^1$ is an optionally substituted aryl;
  $X^1$ is Arg, Dap, Dab, Orn, Lys, Dap(iPr), Dab(iPr), Orn(iPr), or Lys(iPr); each of $AA^3$ is independently Gly, Phe, 2Nal, 1Nal, Arg, Dap, Dab, Orn, Lys, Dap(iPr), Dab(iPr), Orn(iPr), Lys(iPr);
  and wherein at least one of $AA^1$, $X^1$, $AA^2$, or $AA^3$ comprises a moiety of the formula:
  wherein
    $L^1$ is a polymeric linker having a functional group for linking Q, wherein $L^1$ comprises from about 2 to about 20 monomers or copolymers;

Q is absent, AA$^4$, or a moiety of the formula:
-[AA$^4$-Y$^1$-L$^2$]$_c$-Y$^2$-Z,
wherein
  c is 0 or 1;
  AA$^4$ is an amino acid or a derivative thereof;
  Y$^1$ is a side-chain function group of amino acid AA$^4$;
  L$^2$ is a non-polymeric linker;
  Z a medically useful compound; and
  Y$^2$ is a functional group of said medically useful compound or a functional group of L$^2$;
and wherein one or more of AA$^1$, AA$^2$, X$^1$, AA$^3$, and AA$^4$ are optionally isotopically labelled.

The medically useful compounds that can be used in the invention include, but are not limited to, compounds that can be used in diagnosis, treatment, or assaying various clinical conditions. Exemplary medically useful compounds include, but are not limited, imaging agents, contrast agents, and therapeutic agents (e.g., drugs).

In some embodiments, the selective CXCR4 binding peptide conjugate of the invention is of the formula:

(SEQ ID NO: 2)

IA

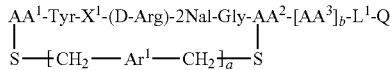

AA$^1$-Tyr-X$^1$-(D-Arg)-2Nal-Gly-AA$^2$-[AA$^3$]$_b$-L$^1$-Q
|                                                  |
S—{CH$_2$——Ar$^1$——CH$_2$}$_a$—S wherein a, b, AA$^1$, X$^1$, AA$^2$, AA$^3$, L$^1$, Q, and Ar$^1$ are those defined herein. Throughout this disclosure, the terms "those defined herein" and "those defined above" when referring to a variable incorporates by reference the broad definition of the variable as well as any narrower definitions including preferred, more preferred and most preferred definitions, if any.

In some embodiment, Q is absent from compounds of formulas disclosed herein. In this manner, at least one of AA$^1$, X$^1$, AA$^2$, or AA$^3$ comprises a moiety of the formula -L$^1$. Such a compound can be used as a starting material for attaching or linking AA$^4$, -AA$^4$-Y$^1$-L$^2$, or a moiety of the formula: -[AA$^4$-Y$^1$-L$^2$]$_c$-Y$^2$-Z.

Still in other embodiments, Q is AA$^4$. Such a compound can be used for attaching or linking a moiety of the formula -Y$^1$-L$^2$-Y$^2$-Z.

Yet in other embodiments, Q is a moiety of the formula: -[AA$^4$-Y$^1$-L$^2$]$_c$-Y$^2$-Z. Thus, the invention provides both starting materials for attaching a medically useful compound as well as selective CXCR4 binding peptide conjugates that include at least one medically useful compound.

In other embodiments, a is 0. Still in other embodiments, a is 1.

Yet still in other embodiments, at least one of X$^1$ and AA$^3$ is isotopically labelled. In other embodiments, both X$^1$ and AA$^3$ are isotopically labelled. Exemplary isotopic labels include, but are not limited to, deuterium, tritium, $^{13}$C, $^{14}$C, $^{18}$O, and a combination thereof. In one particular embodiment, isotopic label comprises deuterium or tritium. Typically, the isotopically labelled X$^1$ and/or AA$^3$ comprises deuterium, tritium, $^{13}$C, $^{14}$C, $^{18}$O, or a combination thereof. In one particular embodiment, at least one of X$^1$ and AA$^3$ is isotopic labelled with deuterium or tritium. In one specific embodiment, X$^1$ and AA$^3$ are isotopically labelled Lys(iPr). More specifically, in one embodiment, X$^1$ and AA$^3$ are both Lys(deuterated iPr).

Still yet in other embodiments, the medically useful compound is a therapeutic agent. In some embodiments, the therapeutic agent is an anticancer agent. Exemplary anticancer agents that can be used in the invention include, but are not limited to, paclitaxel, Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbestrol, Eribulin, Ethinyl, estradiol, Etoposide, Mitomycin, Mitotane, Mitoxantrone, Pentastatin, Pipobroman, Plicamycin, Prednisone, Procarbazine, Streptozocin, Tamoxifen, Teniposide, Vinblastine, and Vincristine. In general, any anticancer agent that has a functional group suitable for linkage can be used. Such anticancer agents will be readily apparent to one skilled in the art having read the present disclosure.

In other embodiments, the selective CXCR4 binding peptide conjugate of the invention of the formula:

(SEQ ID NO: 3)

IB

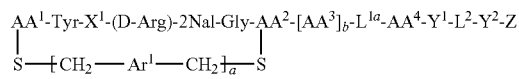

AA$^1$-Tyr-X$^1$-(D-Arg)-2Nal-Gly-AA$^2$-[AA$^3$]$_b$-L$^{1a}$-AA$^4$-Y$^1$-L$^2$-Y$^2$-Z
|                                                                |
S—{CH$_2$——Ar$^1$——CH$_2$}$_a$—S wherein a, b, AA$^1$, X$^1$, AA$^2$, AA$^3$, AA$^4$, Y$^1$, Y$^2$, L$^2$, Z, and Ar$^1$ are those defined herein; and Lia is a polymeric linker comprising from about 2 to about 20 monomers or copolymers.

Yet in some embodiments, L$^2$ is a non-polymeric linker of the formula: —CH$_2$—C(=O)—NH—CH$_2$—, —CH$_2$—NH—C(=O)—CH$_2$—, —(CH$_2$)$_n$—C(=O)—NH—CH$_2$—, —(CH$_2$)$_n$—NH—C(=O)—CH$_2$—, or —(CH$_2$)$_n$—, wherein n=is an integer from 1 to 6.

Still in other embodiments, AA$^1$ along with the sulfur atom that is attached thereto is optionally substituted cysteine or optionally substituted homocysteine. For example, the α-amino group of AA$^1$ can be substituted with an acyl group (e.g., acetyl group, etc.), alkyl group (e.g., methyl, dimethyl, ethyl, dimethyl, propyl, dipropyl, iso-propyl, di(iso-propyl), etc.), haloalkyl (e.g., trifluoromethyl, ditrifluoromethyl, etc.). Other suitable substituents for AA$^1$ will be readily apparent to one skilled in the art having read the present disclosure.

Similar to AA$^1$, AA$^2$ along with the sulfur atom that is attached thereto can also be an optionally substituted cysteine or optionally substituted homocysteine.

In one particular embodiment, X$^1$ and/or at least one of AA$^3$ is Lys(iPr) or Lys(deuterated-iPr). When deuterated (e.g., "deuterated-iPr"), iso-propyl group ("iPr") can have one or more hydrogen atom that is replaced with a deuterium. In some embodiments, at least 2, typically at least 3, often at least 4, more often at least 5 and most often at least 6 hydrogen atoms of iPr are replaced with deuterium atoms. Throughout this disclosure, a short hand notation for amino acids AA(X) refers to amino acid AA that is substituted with "X" on the side chain functional group. For example, Lys(iPr) refers to lysine that is substituted with iso-propyl group on the amine functional group of lysine's side chain.

Yet other embodiments of the invention, Ar$^1$ is phenyl. In one particular embodiment, Ar$^1$ is of the formula:

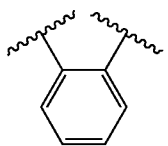 [SMILES: *c1ccccc1*]

Still in another particular embodiment of the invention, b is 1. Within this embodiment, in some instances, b is 1 and $AA^3$ is Lys(iPr) or Lys(deuterated-iPr).

In another embodiment of the invention, $L^1$ is a polymeric linker of the formula: —NH—$(CH_2)_2$—[O—$CH_2$—$CH_2$-$]_n$-O—$(CH_2)_2$—C(=O)—, wherein n is an integer from 2 to 20, typically, from 2 to 15, often from 2 to 10, still more often from 2 to 8, yet more often from 2 to 6, and most often 3 to 6. In some instances, —NH— is attached to the carbonyl carbon of amino acid $AA^3$. Still in other instances, —C(=O)— is attached to α-amino functional group of amino acid $AA^4$.

In one particular embodiment, $AA^4$ is cysteine, homocysteine, or penicillin amine.

Still in other embodiments, at least one of $AA^1$, $X^1$, $AA^2$, or $AA^3$ amino acid residue is a (D)-isomer.

Yet in other embodiments, a is 0.

In yet other embodiments, $AA^1$ is homocysteine.

Exemplary selective CXCR4 binding peptide conjugates of the invention include, but are not limited to, Compound of Formula A, Compound of Formula B, Compound of Formula C, Compound of Formula D, Compound of Formula E, Compound of Formula F, Compound of Formula G, Compound of Formula H, Compound of Formula I, Compound of Formula J, Compound of Formula K, Compound of Formula L, Compound of Formula M, Compound of Formula N, Compound of Formula O, and Compound of Formula P, as well as the corresponding deuterium labelled compounds (i.e., -D12) and tritium labelled compounds (i.e., -T12).

Another aspect of the invention provides a method for treating a subject suffering from a cancer, said method comprising administering to the subject a therapeutically effective amount of a selective CXCR4 binding peptide conjugate disclosed herein, wherein said medically useful compound is an anticancer agent. Exemplary anticancer agents used methods of the invention include, but are not limited to, paclitaxel, Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbestrol, Eribulin, Ethinyl, estradiol, Etoposide, Mitomycin, Mitotane, Mitoxantrone, Pentastatin, Pipobroman, Plicamycin, Prednisone, Procarbazine, Streptozocin, Tamoxifen, Teniposide, Vinblastine, and Vincristine.

In some embodiments, methods of the invention provide treatment of cancer selected from the group consisting of breast cancer, lung cancer, pancreatic cancer, kidney cancer, brain cancer, blood cancer, leukemia, prostate cancer, ovarian cancer, and bladder cancer.

DETAILED DESCRIPTION OF THE INVENTION

CXCR4 plays an important role in immune and inflammatory responses in various diseases and disorders, including cancer, viral infections, as well as autoimmune pathologies such as rheumatoid arthritis. The present invention is based at least in part on reducing or preventing overexpression or activation of CXCR4 to treat, diagnose or image a clinical condition associated with CXCR4 overexpression and/or activation. As used herein, the term "overexpression and/or activation" refers to expression of a gene above its normal (i.e., control) or baseline level and/or activation of CXCR4 above its normal, control or baseline level, respectively.

The terms "normal," "baseline level" and "control level" are used interchangeably herein and refer to expression and/or activity level of CXCR4 in subject(s) that do not have a disease or a clinical condition associated with overexpression and/or activation of CXCR4, such as those disclosed herein. In some embodiments, the baseline level can be a normal level, meaning the level in a sample from a normal subject that do not have a clinical condition associated with overexpression and/or activation (or activity) of CXCR4. This allows a determination based on the baseline level of CXCR4 expression or its biological activity, i.e., whether a sample to be tested or evaluated for disease or a clinical condition has a measurable increase, decrease, or substantially no change in CXCR4 expression or activation as compared to the baseline level.

It should be appreciated that the overexpression and/or activation of CXCR4 can also be determined by comparing the sample result with a positive control. The term "positive control" as used herein refers to a level of CXCR4 expression and/or activation (or activity) established in a sample from a subject or from a population of individuals, where the sample was believed, based on data from that sample, to have a disease or a clinical condition associated with overexpression and/or activation of CXCR4 (e.g., cancer, autoimmune disease such as rheumatoid arthritis and viral infection, such as HIV infection).

In other embodiments, the baseline level can be established from a previous sample from the subject being tested, so that the disease progression or regression of the subject can be monitored over time and/or the efficacy of treatment can be evaluated.

Some aspects of the invention provide compounds that have a high affinity toward CXCR4 that is attached to a diagnostic agent, a therapeutic agent or an imaging agent, through a linker. Such compounds include a CXCR4 binding moiety and a medically active component (or simply "an active compound"). As used herein, the term "medically active compound" refers to a compound that is a therapeutically active, or can be used in diagnostic or imaging, or any other uses associated with treatment, diagnostic, imaging, analysis or other uses in clinical applications. The invention also provides methods for using the same, e.g., in targeted delivery of therapeutics to treat clinical conditions manifested by or associated with overexpression and/or activation of CXCR4, imaging (e.g., in vivo or in vitro) cells associated with CRCR4, identifying cells overexpressing or cells having activated CXCR4, etc. As used herein, the term "high affinity" or "selective" means the compound or the moiety that binds to CXCR4 has a binding constant ($K_b$) of about 10 nM or less, typically about 3 nM or less, and often 1 nM or less. Alternatively, the term "high affinity" or "selective" means the compound or the moiety that binds to CXCR4 has 50% binding inhibition concentration ($IC_{50}$) of about 30 nM or less, typically about 10 nM or less and often about 3 nM or less. Methods for determining binding constant and $IC_{50}$ are well known to one skilled in the art. See, for example, commonly assigned U.S. provisional patent application No. 62/384,132, filed Sep. 6, 2016, and 62/505,064, filed May 11, 2017, and commonly assigned PCT patent application no. PCT/US17/50106, filed Sep. 5, 2017, all of which are incorporated herein by reference in their entirety. In particular, the values $K_b$ and $IC_{50}$ are determined using the CXCR4/$^{125}$I-SDF-1α binding assay described in the above referenced provisional patent applications.

When referring to a numerical value, the term "about" and "approximately" are used interchangeably herein and refer to being within an acceptable error range for the particular value as determined by one of ordinary skill in the art. Such a value determination will depend at least in part on how the value is measured or determined, e.g., the limitations of the measurement system, i.e., the degree of precision required for a particular purpose. For example, the term "about" can mean within 1 or more than 1 standard deviation, per the practice in the art. Alternatively, the term "about" when referring to a numerical value can mean±20%, typically ±10%, often ±5% and more often ±1% of the numerical value. In general, however, where particular values are described in the application and claims, unless otherwise stated, the term "about" means within an acceptable error range for the particular value, typically within one standard deviation.

In one particular aspect of the invention, a high affinity or selective CXCR4 binding peptide conjugate ("PC") is of the Formula:

(SEQ ID NO: 1)

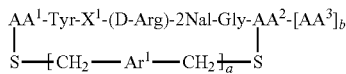

I or a pharmaceutically acceptable salt thereof,
wherein:
a is 0 or 1;
b is an integer from 1 to 4;
$AA^1$ along with the sulfur atom that is attached thereto is 3-mercaptopropionic acid, optionally substituted cysteine, or optionally substituted homocysteine;
$AA^1$ along with the sulfur atom that is attached thereto is 3-mercaptopropionic acid, optionally substituted cysteine, optionally substituted homocysteine, or optionally substituted penicillamine;
$AA^2$ along with the sulfur atom that is attached thereto is cysteine or homocysteine;
$Ar^1$ is an optionally substituted aryl;
$X^1$ is Arg, Dap, Dab, Orn, Lys, Dap(iPr), Dab(iPr), Orn(iPr), or Lys(iPr);
each of $AA^3$ is independently Gly, Phe, 2Nal, 1Nal, Arg, Dap, Dab, Orn, Lys, Dap(iPr), Dab(iPr), Orn(iPr), Lys(iPr);
and wherein at least one of $AA^1$, $X^1$, $AA^2$, or $AA^3$ comprises a moiety of the formula:

-$L^1$-Q, wherein
$L^1$ is a polymeric linker having a functional group for linking Q, wherein $L^1$ comprises from about 2 to about 20 monomers or copolymers;
Q is absent, $AA^4$, or a moiety of the formula:
-[$AA^4$-$Y^1$-$L^2$]$_c$-$Y^2$-Z, wherein
c is 0 or 1;
$AA^4$ is an amino acid or a derivative thereof;
$Y^1$ is a side-chain function group of amino acid $AA^4$;
$L^2$ is a non-polymeric linker;
Z a medically useful compound; and
$Y^2$ is a functional group of said medically useful compound or a functional group of $L^2$;
and wherein one or more of $AA^1$, $AA^2$, $X^1$, $AA^3$, and $AA^4$ are optionally isotopically labelled.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be appreciated that the terms "optionally substituted" when referring to an amino acid, means the side chain functional group of the amino acid or the α-amino group of the amino acid may be substituted, for example, by an alkyl (e.g., $C_1$-$C_{10}$ alkyl) or a functional group protecting group, etc. For example, for lysine or other amino acids having a side chain with a nitrogen heteroatom, optionally substituted or "derivative thereof" includes those substituted with an alkyl, a nitrogen protecting group (e.g., acyl containing moieties), and/or a haloalkyl (e.g., trifluoromethyl, etc.). For cysteine and other sulfur heteroatom containing amino acids (including homocysteine and penicillamine), the terms "optionally substituted" and "derivatives thereof" can include those that are optionally substituted on the sulfur atom or the α-amine functional group, such as those with alkyl, thiol or amine protecting group, etc. Typically, when referring to $AA^1$ and $AA^4$, the term optionally substituted refers to substitution on the α-amine group. Exemplary substitutions on the α-amine group include, but are not limited to, alkyl group, and amine protecting group, as well as those other substituents known to one skilled in the art. "Protecting group" refers to a moiety that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety.

$AA^4$ is an amino acid or a derivative thereof, where $AA^4$ has a side-chain functional group $Y^1$. This presence of the side chain functional group allows attaching linker $L^2$ to the amino acid $AA^4$. It should be appreciated that, while the functional group $Y^1$ when attached to $L^1$ has one less hydrogen atom attached thereto. For example, in lysine the side chain functional group is —$NH_2$, thus $Y^1$ when it is not linked to $L^2$ is —$NH_2$ and when it is linked to $L^2$, $Y^1$ is —NH—. Thus, it should be understood that the number of hydrogen atom attached to or is present on $Y^1$ is omitted merely for brevity. Furthermore, the side-chain functional group of any amino acid can be readily changed by one skilled in the art. For example, the hydroxy side chain functional group of serine can be changed to an amine, carboxylic acid, or other functional groups by one skilled in the art using the known reaction procedures. In addition, amine side chain functional group (i.e., —$NH_2$) of lysine can be changed to azide, —NH—$N_3$, hydroxy, amide, phosphate, thiol, etc.

In one particular embodiment, $X^1$ is optionally isotopically. Still in another embodiment, $AA^3$ is optionally isotopically.

In some embodiments, $X^1$ and/or $AA^3$ are/is isotopically labelled. Isotopically labelled compound of Formula I can be used inter alia for imaging and/or diagnostic purposes. Exemplary isotopically labelled $X^1$ and/or $AA^3$ include those comprising a positron-emitting radioisotope such $^{34}Cl$, $^{45}Ti$, $^{51}Mn$, $^{61}Cu$, $^{63}Zn$, $^{68}Ga$, $^{11}C$, $^{13}N$, $^{15}O$, and $^{18}F$. When radioisotope is used, typically such radioisotopes are complexed to $X^1$ and/or $AA^3$ via a complexing or coordinating agent. Suitable complexing or coordinating moieties are well known to one skilled in the art. Other useful isotopic labels include, but are not limited to, deuterium (D), tritium (T), $^{13}C$, $^{14}C$, $^{18}O$, or a combination thereof.

Another example of a useful imaging agent includes a radioactive metal isotope that is coordinated (i.e., chelated) to a chelating group. Particularly useful radioactive metal isotopes include technetium, rhenium, gallium, gadolinium, indium, copper and a combination thereof. Appropriate chelating groups for a particular radioactive metal isotope are well known to one skilled in the art. For example, ferrocene and its derivatives, ethylenediaminetetraacetic acid ("EDTA"), its derivatives, a peptidyl moiety Dap-Asp-Cys and its derivatives (see U.S. Pat. No. 7,128,893), and others known in the art.

Yet another example of a useful imaging agent includes a contrasting agent. Contrasting agents are widely used, for example, in magnetic resonance imaging (MRI). Wide variety of contrasting agents are known to one skilled in the art including gadobenate, gadobutrol, gadodiamide, gadofosveset, gadopentetate, gadoterate, gadoteridol, gadoversetamide, gadoxetate, and iron oxide.

Still another example of a useful imaging agent includes a fluorescent dye, such as fluorenylmethyloxycarbonyl (FMOC) and its derivatives, an AlexaFluor dye, an Oregon Green dye, a fluoresceins, a BODIPY (boron-dipyrromethene) dye, a cyanine dye, a rhodamine dye, a DyLight dye, and Texas Red.

In other embodiments, $X^1$ and/or $AA^3$ comprises (e.g., attached or linked to) a diagnostic agent, such as an imaging agent, an isotopic agent, or a radioactive agent. In one particular embodiment, $X^1$ and/or $AA^3$ is isotopically labelled. In some instances, $X^1$ and/or $AA^3$ is lysine that is substituted with isotopically labelled side-chain. As used herein, the term "side-chain" or "side chain" when referring to an amino acid is used to describe the "R" group in the following formula: $H_2N$—CH(R)—$CO_2H$. Side chain for a given amino acid is well known to one skilled in the art, for example, the side chain or "R" for glycine is H, for serine it is a moiety of the formula —$CH_2OH$, etc. In other instances, $X^1$ and/or $AA^3$ is lysine in which the side chain functional group amine is substituted with an isotopically labelled alkyl group. As used herein, the term "isotopically labelled alkyl group" means either the carbon or the hydrogen atom(s) in the alkyl group is replaced with a corresponding isotope such as $^{13}C$ and/or $^{14}C$ for carbon atom(s), or deuterium or tritium for hydrogen atom(s). In some instances, the amine nitrogen of the lysine side chain functional group is isotopically labelled with $^{13}N$. Still in other embodiments, the carbonyl oxygen of the amino acid is isotopically labelled with $^{18}O$. Yet in other embodiments, one or more carbon atoms in the amino acid $X^1$ and/or $AA^3$ is isotopically labelled with $^{13}C$ or $^{14}C$. Still in other embodiments, α-amino functional group of amino acid $X^1$ and/or $AA^3$ is isotopically labelled with $^{14}N$. Yet still in other embodiments, α-amino functional group of amino acid $X^1$ and/or $AA^3$ can be substituted with isotopically labelled group, such as isotopically labelled carbonyl group (e.g., $^{18}O$ $^{13}C$, $^{14}C$ labelled carbonyl group) or isotopically labelled alkyl group (e.g., D, T, $^{13}C$, or $^{14}C$).

In one specific embodiment, $X^1$ and/or $AA^3$ is Lys(iPr) or D-Lys(iPr) where one or more, typically two or more, often three or more, more often four or more, still more often five or more and most often at least six hydrogen atoms on the iPr group is isotopically labelled (i.e., replaced with) with deuterium or tritium.

As can be seen in formula I, in one embodiment the peptidyl group is linked to a medically useful compound of the formula Z by using the functional group "$Y^2$" that is present on the medically useful compound or alternatively that is present on linker $L^2$. Such an attachment is well known and can be readily achieved by one skilled in the art. For example, when the functional group $Y^2$ is part of the linker $L^2$, medically useful compound Z is modified such that a leaving group or other suitable bond forming agent is present in Z, e.g., if $Y^2$ is an amino group of $L^2$, it can be used to displace a halide or other suitable leaving groups (e.g., mesylate, tosylate, etc.) or connect to a carbonyl group that is present in the medically useful compound Z to form an amine or amide linkage, respectively. Similarly, if $Y^2$ is a hydroxyl group, it can be used to displace a halide or other leaving group or connect to a carbonyl group that is present in the medically useful compound to form an ether or an ester, respectively. In a similar manner, if the function group $Y^2$ is present on the medically useful compound Z, then $Y^2$ can be used to attach linker $L^2$. For example, by linking a hydroxyl or an amino group that is present on the medically useful compound to a carbonyl group that is present on the non-polymeric linker $L^2$. In this manner, an ester or an amide bond can be formed, respectively, between the medically useful compound and linker L. Other suitable functional groups for Y2 will be readily recognized by one skilled in the art having read to present disclosure.

Still in some embodiments, $L^2$ is a non-polymeric linker of the formula selected from the group consisting of —$CH_2$—C(=O)—, —NH—$CH_2$—, —$(CH_2)_n$—C(=O)—NH—$CH_2$—, —$(CH_2)_n$—NH—C(=O)—$CH_2$—, or —$(CH_2)_n$—, where n is an integer from 1 to 6. In one particular embodiment, $L^2$ is —$CH_2$—C(=O)— and $Y^2$ is O.

In formula I, amino acid $AA^4$ is an amino acid having a side chain with a functional group -$Y^1$. This allows attachment of linker $L^2$ to the heteroatom $Y^1$. Thus, suitable amino acids $AA^4$ include, but are not limited to, serine, cysteine, lysine, arginine, aspartic acid, glutamine, glutamic acid, histidine, proline, threonine, tryptophan, tyrosine, and the like, as well as homologs or derivatives thereof, such as homocysteine, homoserine. In addition, $AA^4$ can also be a non-proteinogenic amino acid, a synthetic amino acid, or an "unnatural amino acid", i.e., an amino acid that does not occur naturally but are well known to one skilled in the art, such as ornithine, 1,4-diaminobutyric acid (Dab), 1,3-diaminopropionic acid (Dap), penicillamine, etc. In one particular embodiment, $AA^4$ is cysteine, homocysteine, or penicillamine. In such instances, $Y^1$ is sulfur (e.g., thiol). In another specific embodiment, $AA^4$ is serine, in which instances $Y^1$ is oxygen (e.g., a hydroxyl group).

Unless otherwise stated or context requires otherwise, amino acids disclosed herein can be either (D)- or (L)-stereo configuration. In fact, in some embodiments, one or more amino acids are (D)-configuration. In this manner, in vivo stability of compound of Formula I can be greatly enhanced or increased. Typically, unless stated otherwise amino acids of the invention are proteinogenic amino acids.

Still in other embodiments, $L^1$ is a polymeric linker comprising from about 2 to about 20, typically from about 2 to about 15, often from about 2 to about 10, more often from about 2 to 8, and most often from about 5 to about 8 monomers or copolymers. Copolymer refers to a linker having two or more different monomeric units. For example, a copolymer can be a polymer that is formed between ethylene glycol propylene glycol units; between ethylene glycol and vinyl alcohol units; between ethylene glycol and vinyl acetate units; as well as other copolymers that are well known to one skilled in the art. It should be appreciated that the two end units of $L^1$ (e.g., one end that is attached to $AA^3$ and the other end unit that is attached to $AA^4$ are functionalized such that it can readily be linked to $AA^3$ and $AA^4$. For example, when $L^1$ is a polyethylene glycol ("PEG"), one end of the PEG that is attached to $AA^3$ can be functionalized as an amine so that it forms an amide bond with $AA^3$. If on the other hand, if the end of the PEG that is attached to $AA^3$ is maintained as a hydroxyl group, then it forms an ester bond with $AA^3$. Similar, if the hydroxyl group of PEG that is attached to $AA^4$ is oxidized to a carboxylic acid moiety, then it forms an amide group with the α-amino functional group of $AA^4$. Or when the hydroxyl group of PEG that is attached to $AA^4$ is replaced with a leaving group (e.g., tosylate, mesylate, halide, etc.), it can form an amino linkage with the α-amino functional group of $AA^4$ by, e.g., a displacement reaction. In this manner, a wide variety of methods are available for linking $L^1$ to $AA^3$ and $AA^4$. In one specific embodiment, $L^1$ is a polyethylene glycol in which the end attached to $AA^3$ is an amino group, thereby forming an amide bond with $AA^3$. In another embodiment, $L^1$ is a polyethylene glycol in which the end that is attached to $AA^4$ is oxidized to a carboxylic acid or similar functional group, thereby forming an amide linkage with the α-amino functional group of amino acid $AA^4$.

In some embodiments, a is 1. In one particular embodiment, $AA^3$ is lysine or a derivative thereof (e.g., the amino group of the side chain is alkylated, acylated, or substituted with an amine protecting group) that is optionally isotopically labelled. In some embodiments, the side chain amino functional group is alkylated with an alkyl group optionally having one or more deuterium or tritium in lieu of hydrogen on the alkyl group. In some embodiments, the side chain amino functional group is acylated that is optionally isotopically labelled, for example, isotopically labelled carbonyl oxygen (e.g., $^{18}O$) and/or isotopically labelled carbonyl carbon (e.g., $^{13}C$ or $^{14}C$), etc. In one particular embodiment, $AA^3$ is lysine having an isopropyl group attached to the side chain amino group. In one specific embodiment, the isopropyl group is optionally isotopically labelled, e.g., with a plurality of deuterium and/or tritium atoms.

In some embodiments, a is 0. In this embodiment, compounds have a disulfide bond to afford the ring system.

Still in other embodiments, $AA^3$ is lysine or a derivative thereof (e.g., the amino group of the side chain is alkylated, acylated, or substituted with an amine protecting group) that is optionally isotopically labelled. In some embodiments, the side chain amino functional group is alkylated with an alkyl group optionally having one or more deuterium or tritium in lieu of hydrogen on the alkyl group. In some embodiments, the side chain amino functional group is acylated that is optionally isotopically labelled, for example, isotopically labelled carbonyl oxygen (e.g., $^{18}O$) and/or isotopically labelled carbonyl carbon (e.g., $^{13}C$ or $^{14}C$), etc. In one particular embodiment, $AA^3$ is lysine having an isopropyl group attached to the side chain amino group. In one specific embodiment, the isopropyl group is optionally isotopically labelled, e.g., with a plurality of deuterium and/or tritium atoms.

Yet in other embodiments, $AA^2$ and the sulfur atom to which it is attached to is cysteine, homocysteine, or penicillamine. Typically, $AA^2$ and the sulfur atom to which it is attached to is cysteine or homocysteine. In one specific embodiment, $AA^2$ and the sulfur atom to which it is attached to is cysteine.

Still in other embodiments, $AA^1$ and the sulfur atom to which it is attached to is 3-mercaptopropionic acid (3-MPA), cysteine, homocysteine, or penicillamine. Typically, $AA^1$ and the sulfur atom to which it is attached to is 3-MPA, cysteine or homocysteine. In one specific embodiment, $AA^1$ and the sulfur atom to which it is attached to is cysteine.

In other embodiments, $Ar^1$ is phenyl. The —S—$CH_2$— groups can be positioned at 1,2-; 1,3-; or 1,4-positions of the phenyl group. In one particular embodiment, the —S—$CH_2$- groups are positioned at 1,2-positions, i.e., the phenyl group is 1,2-disubstituted. In other embodiments, $Ar^1$ is phenyl having one, two, three, or four, typically one, two, or three, often one or two, and most often one substituent(s). Exemplary substituents suitable for $Ar^1$ include, but are not limited to, halides (e.g., F, Cl, I, or Br), $C_1$-$C_{10}$ alkyl (e.g., methyl, ethyl, t-butyl, isopropyl, etc.), $C_1$-$C_{10}$ haloalkyl (e.g., —$CF_3$ etc.), nitro, nitroso, -COnR (where n is 1 or 2 and R is hydrogen or alkyl), cyano, —OR (where R is H, alkyl, carbonyl, etc.), as well as other electron donating or electron withdrawing groups known to one skilled in the art.

Yet in other embodiments, linker $L^2$ comprises a functional group that is capable of releasing $Y^2$-Z in vivo. In this manner, the moiety $Y^2$—Z is released in vivo thereby exerting its therapeutic activity. Suitable functional groups that is capable of releasing $Y^2$-Z depends on the nature of the function group on moiety $Y^2$ that is linked to the linker $L^2$. For example, when the function group on Z is a hydroxyl group (i.e., $Y^2$ is —OH) or an amino group ($Y^2$ is —$NH_2$), the functional group on $L^2$ can be a carboxylate such that an ester bond or an amide bond, respectively, is formed between the medically useful compound and linker $L^2$. If the functional group (i.e., "$Y^2$") on the medically useful compound is a carboxylic acid, the corresponding functional group on $L^2$ can be a hydroxyl group or an amino group to form an ester bond or an amide bond, respectively. Other suitable functional groups on $L^2$ that is capable releasing the medically useful compound in vivo are well known to one skilled in the art including a disulfide bond linkage, an ester linkage, a thiol-maleimide linkage, and the like.

Still yet in other embodiments, the medically useful compound is a therapeutic agent. Suitable therapeutic agents include those that are known to one skilled in the art for treatment of cancer, autoimmune disease (e.g., rheumatoid arthritis), viral infection (e.g., HIV infection), etc. Exemplary therapeutic agents that are useful in compounds of the invention include, but are not limited to, Altretamine; Asparaginase; Bleomycin; Busulfan; Carboplatin; Carmustine; Chlorambucil; Cisplatin; Cladribine; Cyclophosphamide; Cytarabine; Dacarbazine; Diethylstilbestrol; Eribulin, Ethinyl; estradiol; Etoposide; Mitomycin; Mitotane; Mitoxantrone; Paclitaxel; Pentastatin; Pipobroman; Plicamycin; Prednisone; Procarbazine; Streptozocin; Tamoxifen; Teniposide; Vinblastine; Vincristine, daunorubicin, doxorubicin, docetaxel, irinotecan, monomethyl auristatin E, mertansine, SN-38, tesirine, tubulysin, *vinca* alkaloids, and an analog or derivative thereof, HIV protease inhibitors, HIV fusion inhibitors, HIV reverse transcriptase inhibitors, HIV integrase inhibitors, HIV entry inhibitors, and therapeutics for autoimmune diseases.

$L^2$ can be any biocompatible bifunctional linker such as polyethylene glycol (PEG), e.g., in the form of $H_2N-CH_2CH_2\text{-}(PEG)_m\text{-}CH_2CH_2-OOOH$, $HOOC-CH_2CH_2\text{-}(PEG)_m\text{-}CH_2CH_2-COOH$, or $H_2N-CH_2CH_2\text{-}(PEG)_m\text{-}CH_2CH_2-NH_2$, natural and unnatural amino acids or a polyamino acid (PAA), where m is an integer from 0 to 100, typically 1 to 50, often 1 to 25, and more often 1 to 10. Generally, when $L^2$ is a polymer (e.g., PEG, PAA), the total number of monomers within the chain is from about 2 (i.e., a monomer) to about 20, typically from about 2 to about 15, often from about 3 to about 10, and most often from about 4 to about 6.

Still yet in other embodiments, medically useful compound is a diagnostic or imaging agent, such as a radioactive agent, fluorescent agent, etc. Such imaging agents are well known to one skilled in the art. For example, contrast agents for magnetic resonance imaging agents, ultrasound contrast agents, and radio contrast agents. See, for example, en.wikipedia.org/wiki/Contrast_agent.

Still further, combinations of the various groups described herein can form other embodiments. In this manner, a variety of compounds are embodied within the present invention. By combining various groups described herein in different manner, compounds such as those of the formulas IA and IB are included within the scope of the invention:

(SEQ ID NO: 2)

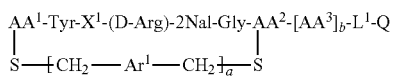

IA where a, b, $AA^1$, $X^1$, $AA^2$, $AA^3$, $L^1$, Q, and $Ar^1$ are those defined herein, and (SEQ ID NO: 3)

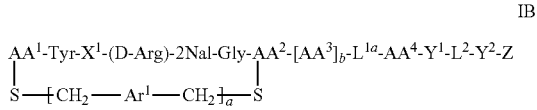

IB where a, b, $AA^1$, $X^1$, $AA^2$, $AA^3$, $AA^4$, $Y^1$, $Y^2$, $L^1$, $L^2$, Z, and $Ar^1$ are those defined herein.

Some specific examples of compounds of the invention include, but are not limited to, Compound of Formula A, Compound of Formula B, Compound of Formula C, Compound of Formula D, Compound of Formula E, Compound of Formula F, Compound of Formula G, Compound of Formula H, Compound of Formula I, Compound of Formula J, Compound of Formula K, Compound of Formula L, Compound of Formula M, Compound of Formula N, Compound of Formula O, and Compound of Formula P, each of which can also be labelled with deuterium (e.g., Compound of Formulas A-D12, B-D12, C-D12, etc.) or tritium (e.g., Compound of Formulas A-T12, B-T12, C-T12, . . . , P-T12). Synthesis of these compounds are provided in the Examples section.

It should be appreciated that throughout this disclosure combinations of different embodiments described herein form other preferred embodiments. For example, one particular embodiment is described herein as "a" being 0, and another embodiment is described herein where $AA^1$ is homocysteine. Thus, combination of these two embodiments provides compound of Formulas I, IA, and IB, where a is 0 and $AA^1$ is homocysteine.

Another aspect of the invention provides a diagnostic kit comprising a high affinity CXCR4 selective binding ligand peptide conjugate described herein where the medically useful compound is a diagnostic agent.

Yet another aspect of the invention provides a composition comprising a compound of Formula I and a pharmaceutically acceptable carrier. Pharmaceutically acceptable carrier can include a diluent, an excipient, a flavoring agent, an adjuvant, a binder, a stabilizer, coloring agent, or a combination thereof. Generally, "pharmaceutically acceptable carrier" refers to any excipient that is useful in preparing a pharmaceutical composition that is generally safe, non-toxic and neither biologically nor otherwise undesirable, and includes excipient that is acceptable for veterinary use as well as human pharmaceutical use.

The present invention includes pharmaceutical compositions comprising at least one compound of the invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively, the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula I, as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula I or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula I and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula I, or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Still another aspect of the invention provides a method for imaging cancer cells in a patient comprising administering to a patient an imaging effective amount of a high affinity CXCR4 selective binding ligand peptide conjugate of Formula I, the medically useful compound is an imaging agent, and imaging cancer cells in said patient using an imaging apparatus. The imaging apparatus used depends on the nature of imaging agent of compound of Formula I. For example, if the imaging agent is a positron-emitting radioisotope, then the imaging apparatus used is a PET scan, and when the medically useful compound is a contrasting agent, then the imaging apparatus can be a computed topography apparatus or an MRI apparatus. When the medically useful compound is a radioactive isotope, the imaging apparatus can be an x-ray machine or other similar device.

One particular aspect of the invention provides a method for treating cancer in a patient. The method comprises administering a therapeutically effective amount of a compound of Formula I (where the medically useful compound is a cancer drug) or a pharmaceutical composition comprising a compound of Formula I (where the medically useful compound is a cancer drug) to a cancer patient.

Another particular aspect of the invention provides a diagnostic or an imaging kit comprising a high affinity CXCR4 selective binding ligand peptide conjugate (PC) of Formula I, where the medically useful compound is a diagnostic agent or an imaging agent, respectively.

Still another particular aspect of the invention provides a method for treating a patient suffering from rheumatoid arthritis, pulmonary fibrosis, HIV infection, or a cancer. The method includes administering a therapeutically effective amount of a compound of Formula I to a patient in need of treatment thereof. In this method, the medically useful compound of compound of Formula I is a therapeutic agent that can be used to treat the particular clinical condition to be treated. Some of the cancers that can be treated using compounds of the invention include, but are not limited to, breast cancer, pancreatic cancer, melanoma, prostate cancer, kidney cancer, neuroblastoma, non-Hodgkin's lymphoma, lung cancer, ovarian cancer, colorectal cancer, multiple myeloma, glioblastoma multiforme, and chronic lymphocytic leukemia.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The following abbreviations are used: Ac: acetyl; Boc: tert-butyloxycarbonyl; BOP: (benzotriazol-1-yloxy)-tris(dimethylamino) phosphonium hexafluorophosphate; Bz: benzoyl; Bzl: benzyl; Dab: 1,4-diaminobutyric acid; Dap: 1,3-diaminopropionic acid; DCC: dicyclohexyl-carbodiimide; DCM: dichloromethane; DIC: diisopropyl carbodiimide; DIEA: diisopropyl-ethylamine; DMAP: 4-(N,N-dimethyl-amino)pyridine; DMF: N,N-dimethyl formamide; DMSO: dimethyl-sulfoxide; EDT: 1,2-ethane-dithiol; Et: ethyl; Fmoc: 9-fluor-enylmethoxy carbonyl; HATU: N-[(dimethylamino)-1H-1,2,3-triazolo[4,5-b]pyridin-1-ylmethylene]-N-methylmethanaminium hexafluorophosphate N-oxide; HBTU: O-benzo-triazolyl-N,N,N',N'-tetramethyluronium hexafluorophosphate; HCTU: 1H-benzotriazo-lium 1-[bis(dimethylamino)methylene]-5-chloro-3-oxide hexafluorophosphate; HOBt: hydroxybenzotriazole; hCys: homocysteine; iPr: isopropyl; IPA: isopropyl alcohol; Me: methyl; Mmt: 4-mthoxytrityl; Mpa: 3-mercaptopropionic acid; 2Nal: 2-naphthylalanine; 1Nal: 1-naphthylalanine; NMM: N-methylmorpholine; NMP: N-methyl-pyrrolidone; Orn: ornithine; Pbf: 2,2,4,6,7-pentamethyl-dihydrobenzofurane-5-sulfonyl; PBS: phosphate buffered saline; PyBOP: (benzotriazol-1-yloxy)-tris(pyrrolidino)-phosphonium hexafluoro-phosphate; PyBrOP: bromotris(pyrrolidino) phosphonium hexafluorophosphate; tBu: tert-butyl; TFA: trifluoroacetic acid; TFE: trifluroethanol; THF: tetrahydrofuran; TIS: triisopropyl silane; Trt: trityl; mini-PEG6: 6-mer of ethylene glycol; all common amino acids are expressed as three letter symbols or otherwise specified.

Mass Spectroscopy (MS) Analysis: Preparation of compounds of the present invention as described in the following examples is meant to be illustrative rather than limiting. In each of these examples, the observed molecular weight is reported as a de-convoluted value. The de-convoluted value is derived from the formula MW (observed)=n(m/z)−n, where m/z represents the charged ion (positive mode) and n is the number of charges of the specific species. When multiple charged species are present in the mass spectrum, the observed molecular weight is reported as an average.

General Method of Peptide Synthesis, Cyclic Structure Formation, and Salt Exchange: Peptides were synthesized using solid phase peptide synthesis chemistry known in the art. The cyclic structure of those peptides was established, for a disulfide, by using air oxidation, or iodine oxidation in the presence of acidic acid, or for a bisthioether ring, by nucleophilic substitution using a bis(halomethyl) aryl compound, typically using 1.3 equivalents of a bis(bromomethyl) aryl compound, in the presence of a base, such as 15 mM ammonium bicarbonate solution.

While the present invention illustrates preparation of one particular peptide linkage, other peptide linkages that are within the scope of the present invention can be readily prepared using procedures disclosed in, for example, commonly assigned U.S. patent application Ser. No. 15/898,434, filed Feb. 17, 2018, and Ser. No. 15/695,862, filed Sep. 5, 2017, both of which are incorporated herein by reference in their entirety. Furthermore, other peptides linkages that are within the scope of the present invention can readily be prepared by one skilled in the art having read the present disclosure along with the commonly assigned U.S. patent applications that are incorporated by reference herein.

Paclitaxel Activation—Preparation of 2'-maleimide-paclitaxel:

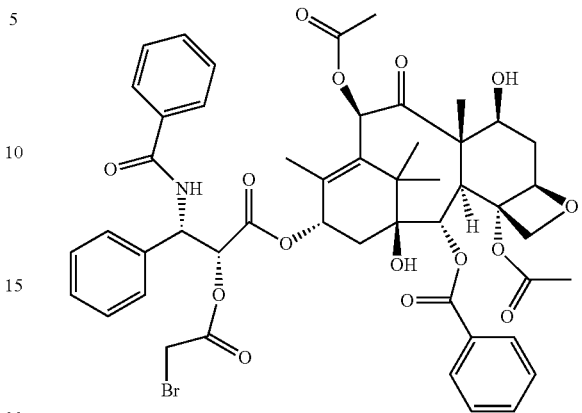

To a 0° C. solution of 500 mg of paclitaxel (0.6 mmole) in 80 mL of DCM and 0.06 mmole of DMAP (9.2 mg) was added a solution of 1.1 mmole of 2-bromoacetic acid (100.3 mg) in 50 mL of DCM followed by 3 eq. of DIC (0.3 mL) under stirring. The reaction mixture was then slowly warmed up to room temperature and the coupling reaction was allowed to proceed at 30° C. for one hour under continuous stirring. Crude product of 2'-bromoacetyl-paclitaxel was purified and lyophilized before conjugation to cyclized CXCR4 antagonist peptide (MW MS: observed 975.10; calculated: 974.85).

Purification, Salt Form Conversion, and Final Product Characterization: Final products were purified by reverse phased HPLC and further characterized by analytical HPLC and mass spectroscopy. Peptides purified from reverse phased HPLC were usually in trifluoroacetic acid (TFA) form. This salt was typically converted to a more pharmaceutically friendly salt form, such as acetic acid or hydrochloric acid salt form. Converting a peptide in TFA salt to a hydrochloric acid salt could be achieved by repeated lyophilization of the peptide in TFA salt in a dilute hydrochloric acid solution. For conversion of a peptide in TFA salt to an acetate salt, typically the following process was used. Strong anion exchange resin (chloride form, substitution 3 mmole/g, water content 50%, using 2 grams of resin per gram of peptide) was first washed three times with milli Q water, then three times with 1 N NaOH solution three times, 5 min/time, and then five times with milli Q water, 5 min/time. The resin was further washed with 75% ethanol water until the pH reaches about 7.4. This resin was treated with 10% acetic acid solution three times, five minutes each time. The resin was then washed with 1% acetic acid solution three times, five minutes each time. The resin was ready for the salt conversion of the purified peptide.

The purified, lyophilized peptide was dissolved in 1% acetic acid solution and added to the prepared resin described above. The mixture was agitated or magnetically stirred at room temperature for 1 h. The supernatant was separated. The resin was washed three times with 1% acetic acid solution. The supernatant and the washing solution were combined, filtered through a 0.22 μm membrane and lyophilized, to afford a peptide in acetate salt.

Example 1: Synthesis of Compound A
(SEQ ID NO: 4)
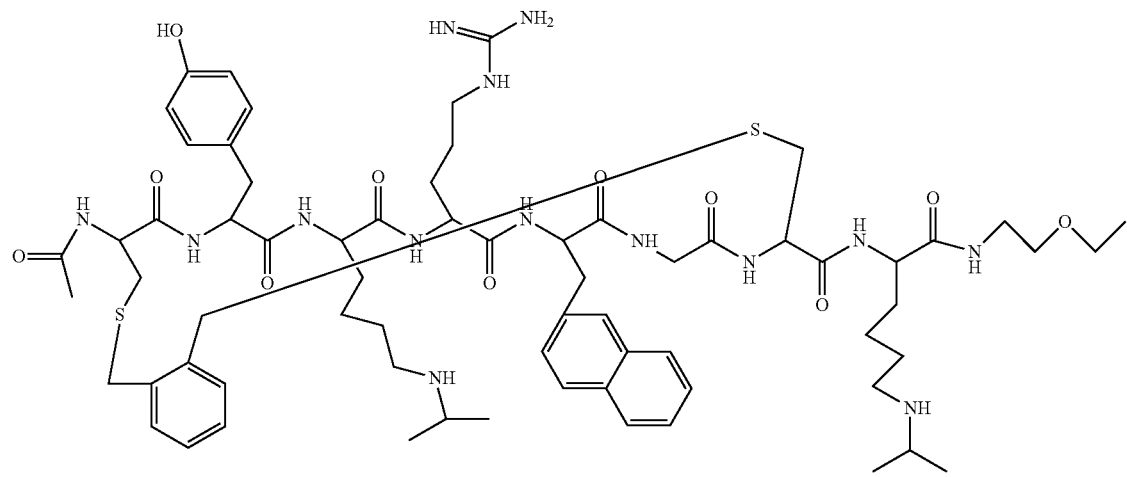
Compound A
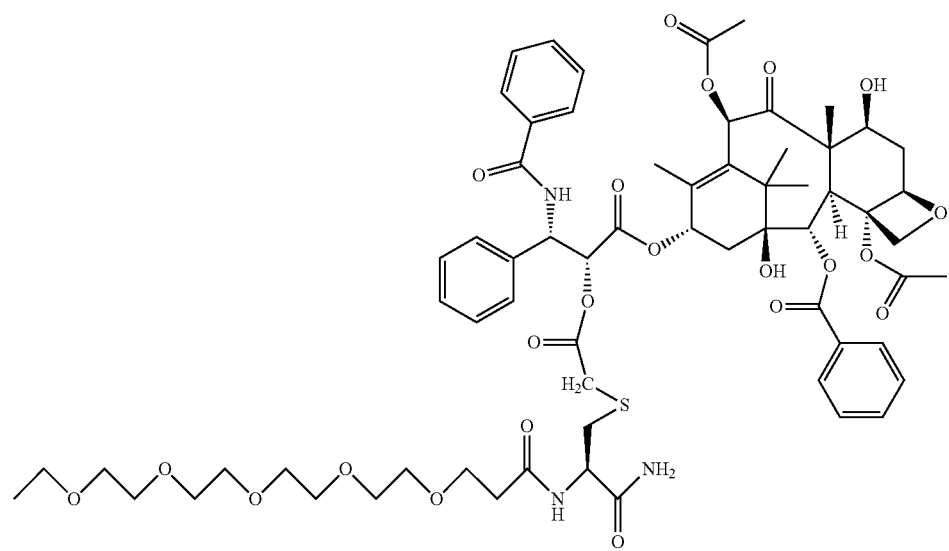

Peptide chain assembly: Fmoc-Cys(Mmt)-Tyr(tBu)-Lys(iPr,Boc)-(D-Arg(Pbf))-2Nal-Gly-Cys(Mmt)-Lys(iPr,Boc)-(mini-PEG6)-Cys(Trt)-Sieber Amide AM Resin (SEQ ID NO:5)

(SEQ ID NO: 6)

Compound B

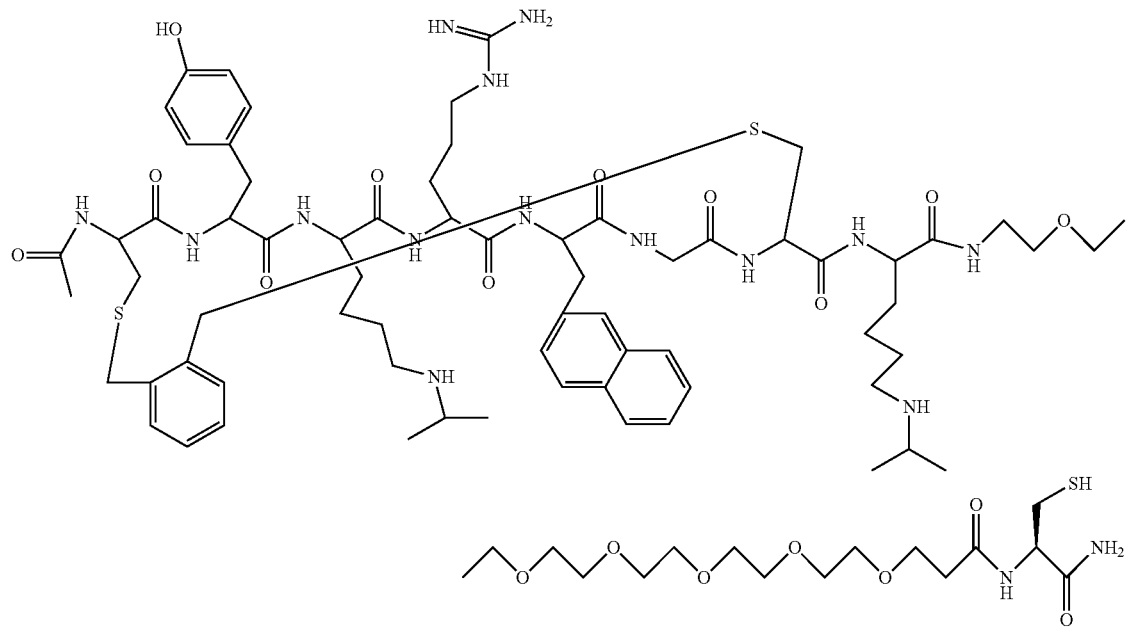

The peptide chain was assembled by standard Fmoc chemistry using Sieber amide AM resin (Xi'an LanXiao Chemical Limited, Xi'an, China). Briefly, 40 g of Sieber amide AM resin was swollen in 300 mL of DCM for 2 h and then washed four times with DMF. Removal of Fmoc was carried out in 250 mL of 200% piperidine in DMF for 20 min at room temperature and washed several times with DMF. Ninhydrin test was negative. Stepwise chain assembly started with Fmoc-Cys(Trt)-OH from the C-terminal end of the linear peptide. Three equivalents of protected amino acid Fmoc-Cys(Trt)-OH were activated with DIC/HOBt in 80 mL of DMF, and coupled to the Fmoc-removed Sieber amide AM resin prepared above for 2 h at room temperature. Ninhydrin test was negative. Capping of the non-reacted amino group was performed for 30 min with 160 mL of a mixture of acetic anhydride/DIEA/DCM at a volume ratio of 1:1:4. This was followed by Fmoc removal using 250 mL of 20% o piperidine in DMF for 20 min. The following residues were coupled sequentially without capping: Fmoc-(mini-PEG6)-OH, Fmoc-Lys(iPr,Boc)-OH, Fmoc-Cys(Mmt)-OH, Fmoc-Gly-OH, Fmoc-2Nal-OH, Fmoc-D-Arg(Pbf))-OH, Fmoc-Lys(iPr,Boc)-OH, Fmoc-Tyr(tBu)-OH, and Fmoc-Cys(Mmt)-OH. After the coupling of last residue Fmoc-Cys (Mmt), Fmoc protection was removed again using 250 mL of 20% piperidine in DMF for 20 min. N-terminal acetylation was carried out with 160 mL of a mixture of acetic anhydride/DIEA/DMF (1:1:4, v/v/v) for 30 min at room temperature. The resin was then washed with 250 mL of DMF three time and then with 250 mL of DCM three times, then dried under vacuum to afford 81 grams of peptide resin containing the assembled target linear peptide. The dried resin was divided into several portions and one portion (20 grams) is used in the following operation.

Removal of Mmt protection on Cys residues and Cleavage of partial protected linear peptide from peptide resin: 20 grams of above peptide resin was swelled in 300 mL of DCM for 30 min. Total 1000 mL of a cleavage/deprotection cocktail (TFA/H$_2$O/EDT/TIS/DCM, 6:3:1.5:3:86.5, v/v) was added to above swelled resin to remove Mmt protection of Cys side chain. The mixture was stirred for 20 min at room temperature. This deprotection and cleavage procedure was repeated once using another 1000 mL of the cleavage/deprotection cocktail above at room temperature for 20 min. After removal of the solid resin by filtration, the cleavage solutions containing the partially deprotected linear peptide were combined and concentrated under vacuum using a rotary evaporator. The residues (crude peptide) were then lyophilized to afford 9.5 grams of partially deprotected crude linear peptide.

Cyclization: To a solution of 2.2 grams of above crude linear peptide in 110 mL of DMF was added 20 mL of MeCN containing 368 mg of 1,2-bis(bromomethyl) benzene. The solutions were mixed well, then 1630 mL of MeCN and 440 mL of water were added. The pH of this reaction mixture was adjusted to pH 8~9 using 1 M of ammonium carbonate solution. The cyclization reaction was allowed to proceed for 1 h at room temperature. The reaction was monitored by MS. The reaction mixture was then divided into six equal portions and lyophilized.

Side chain deprotection of the cyclized peptide: The lyophilized crude cyclized peptide was deprotected using a cleavage cocktail (TFA/EDT/TIS/H$_2$O/thioanisole/phenol, per 100 mL of solution contains 81.5 mL TFA, 2.5 mL EDT, 1.5 mL TIS, 5.0 mL H$_2$O, 5.0 mL thioanisole, and 5.0 grams phenol) at 10 mL each container, for 60 min at 30° C. To the cleavage mixture was added 4 volumes of cold ethyl ether. The crude peptide precipitates were separated by centrifugation at 3000 rpm for 2 min. The crude peptide precipitates were washed three times with ethyl ether. The crude peptide was purified to a purity>90% on preparative HPLC, and lyophilized (MW MS: observed 1719.55; calculated: 1720.18).

Preparation of PDC CXCR4 peptide-paclitaxel drug Conjugate: Above prepared 452 mg of 2'-bromoacetyl-paclitaxel and 905 mg of cyclized CXCR4 peptide were dissolved in 100 mL of MeCN/water (1:1, v/v). The solution was adjusted to pH 7~7.5 using 0.5M of ammonium bicarbonate. The conjugation reaction was completed in about half an hour as confirmed by MS at room temperature. The final product was purified using a reverse-phased preparative column Daisogel (50×250 mm, 8 μm); mobile phases—Solvent A: 0.1% TFA water; Solvent B: 0.1% TFA acetonitrile. Fractions containing the target product MB1707 were combined and lyophilized (a TFA salt). Salt exchange as described above afforded a peptide in acetate salt. Analytical HPLC purity of the final peptide product is 99.61%; MW cal.: 2614.12 Da; MW obs.: 2613.30 Da.

Example 2: Synthesis of Isotopically Labelled Compound A-D12

Peptide chain assembly: Fmoc-Cys(Mmt)-Tyr(tBu)-Lys(Boc)-(D-Arg(Pbf))-2Nal-Gly-Cys(Mmt)-Lys(Boc)-(mini-PEG6)-Cys(Trt)-Sieber Amide AM Resin (SEQ ID NO:7).

Capping of the non-reacted amino group was performed for 30 min with 16 mL of a mixture of acetic anhydride/DIEA/DCM at a volume ratio of 1:1:4. Ninhydrin test was negative. This was followed by Fmoc removal using 25 mL of 20% piperidine in DMF for 20 min.

The following residues were coupled sequentially without the capping step: Fmoc-(mini-PEG6)-OH, Fmoc-Lys(Boc)-OH, Fmoc-Cys(Mmt)-OH, Fmoc-Gly-OH, Fmoc-2Nal-OH, Fmoc-D-Arg(Pbf))-OH, Fmoc-Lys(Boc)-OH, Fmoc-Tyr(tBu)-OH, and Fmoc-Cys(Mmt)-OH. After the coupling of last residue Fmoc-Cys(Mmt), Fmoc protection was removed again using 25 mL of 20% piperidine in DMF for 20 min. N-terminal acetylation was carried out with 16 mL of a mixture of acetic anhydride/DIEA/DMF (1:1:4, v/v/v) for 30 min at room temperature. The peptide resin was then washed with 25 mL of DMF three time and followed by 25 mL of DCM three times, then the peptide resin dried under vacuum to afford 2.8 grams of peptide resin containing the assembled target linear peptide.

(SEQ ID NO: 8)

Compound B-D12

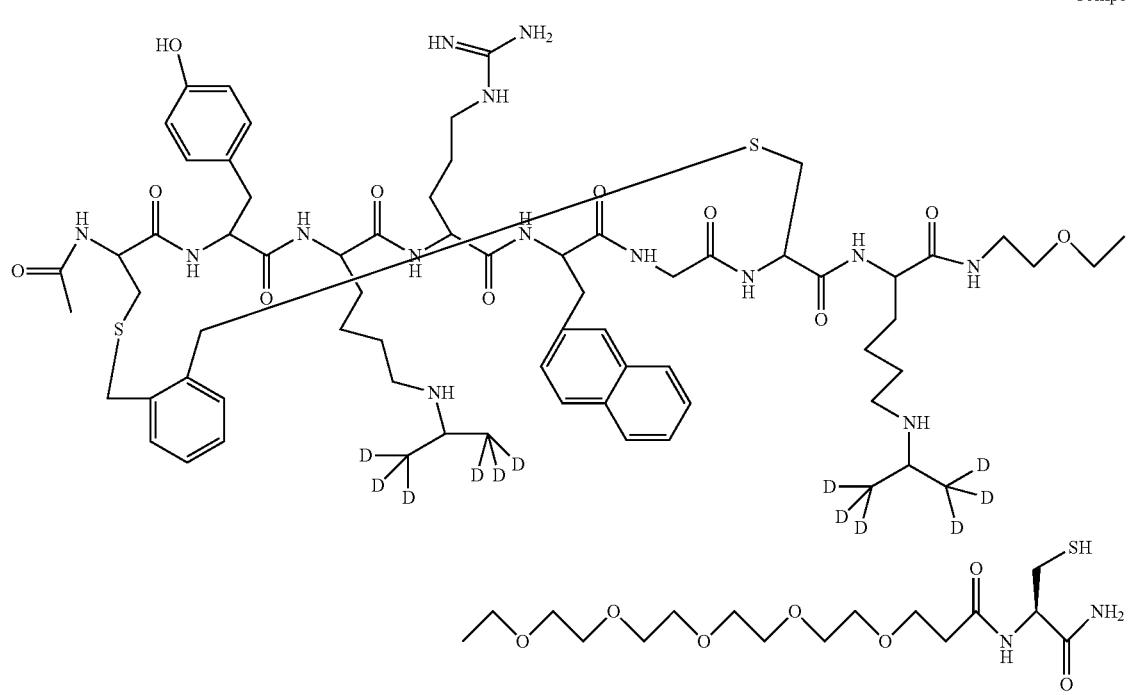

The peptide chain was assembled by standard Fmoc chemistry using Sieber amide AM resin (Xi'an LanXiao Chemical Limited, Xi'an, China). Briefly, 1.5 grams of Sieber amide AM resin was swollen in 30 mL of DCM for 2 h and then washed four times with 25 mL of DMF. Removal of Fmoc was carried out in 25 mL of 20% piperidine in DMF for 20 min at room temperature and washed several times with DMF. Ninhydrin test was negative. Stepwise chain assembly started with Fmoc-Cys(Trt)-OH from the C-terminal end of the linear peptide. Three equivalents of protected amino acid Fmoc-Cys(Trt)-OH (702 mg) were activated with DIC (1 mL)/HOBt (243 mg) in 5 mL of DMF, and coupled to the Fmoc-removed Sieber amide AM resin prepared above in a temperature controlled oven at 30° C. overnight. The reaction mixture was drained and the resin was washed several times with 25 mL of DMF.

Removal of Mmt protection on Cys residues and Cleavage of partial protected linear peptide from peptide resin: 2.8 grams of above peptide resin was swelled in 30 mL of DCM for 30 min. 150 mL of a cleavage/deprotection cocktail (TFA/H$_2$O/EDT/TIS/DCM, 6:3:1.5:3:86.5, v/v) was added to above swelled resin to remove Mmt protection of Cys side chain, 20 min at room temperature. The supernatant of the cleavage mixture was drained into a flask containing 150 mL of water. This deprotection and cleavage procedure was repeated once using another 150 mL of the cleavage/deprotection cocktail above at room temperature for 20 min. After removal of the solid resin by filtration, the cleavage solutions containing the partially deprotected linear peptide were combined and concentrated under vacuum using a rotary evaporator. The residues (crude peptide) were then lyophilized to afford 1.2 grams of partially deprotected crude linear peptide.

Cyclization: To a solution of 1.2 grams of above crude linear peptide in 60 mL of DMF was added 10 mL of MeCN containing 200 mg of 1,2-bis(bromomethyl) benzene. The solutions were mixed well, then 890 mL of MeCN and 240 mL of water were added. The pH of this reaction mixture was adjusted to pH 8~9 using 1 M of ammonium carbonate solution. The cyclization reaction was allowed to proceed for 1 h at room temperature under magnetic stirring. The completion of cyclization was confirmed by MS. The reaction mixture was then divided into three equal portions and lyophilized in a flask.

Side chain deprotection of cyclized peptide: To each of the lyophilized crude cyclized peptide flask was added 10 mL of a cleavage cocktail composed of TFA/EDT/TIS/H$_2$O/thioanisole/phenol (per 100 mL of solution contains 81.5 mL TFA, 2.5 mL EDT, 1.5 mL TIS, 5.0 mL H$_2$O, 5.0 mL thioanisole, and 5.0 grams phenol). The cleavage reaction was allowed to proceed for 60 min at 30° C. To the cleavage mixture was added 4 volumes of cold ethyl ether. The crude peptide precipitates were separated by centrifugation at 3000 rpm for 2 min. The crude peptide precipitates were washed three times with icy cold ethyl ether. The crude peptide was dried under vacuum and then used for lysine side chain modification as following without further purification.

Lysine side chain modification using acetone-D6: 125 mg of crude product from above was dissolved in 12.5 mL of a solution composed of acetic acid:acetone-D6:ethanol (2:2:8.5, v/v), then 324 mg of sodium cyanoboronhydride (NaBH$_3$CN) was added under stirring. The reductive amination was allowed to proceed at 30° C. for 2 h. The reaction mixture was diluted with water and loaded onto a preparative HPLC column. The isotopically labeled cyclic peptide was purified to a purity>90% and lyophilized.

Preparation of PDC—CXCR4 Peptide-Paclitaxel Drug Conjugate:

(SEQ ID NO: 9)

Compound A-D12

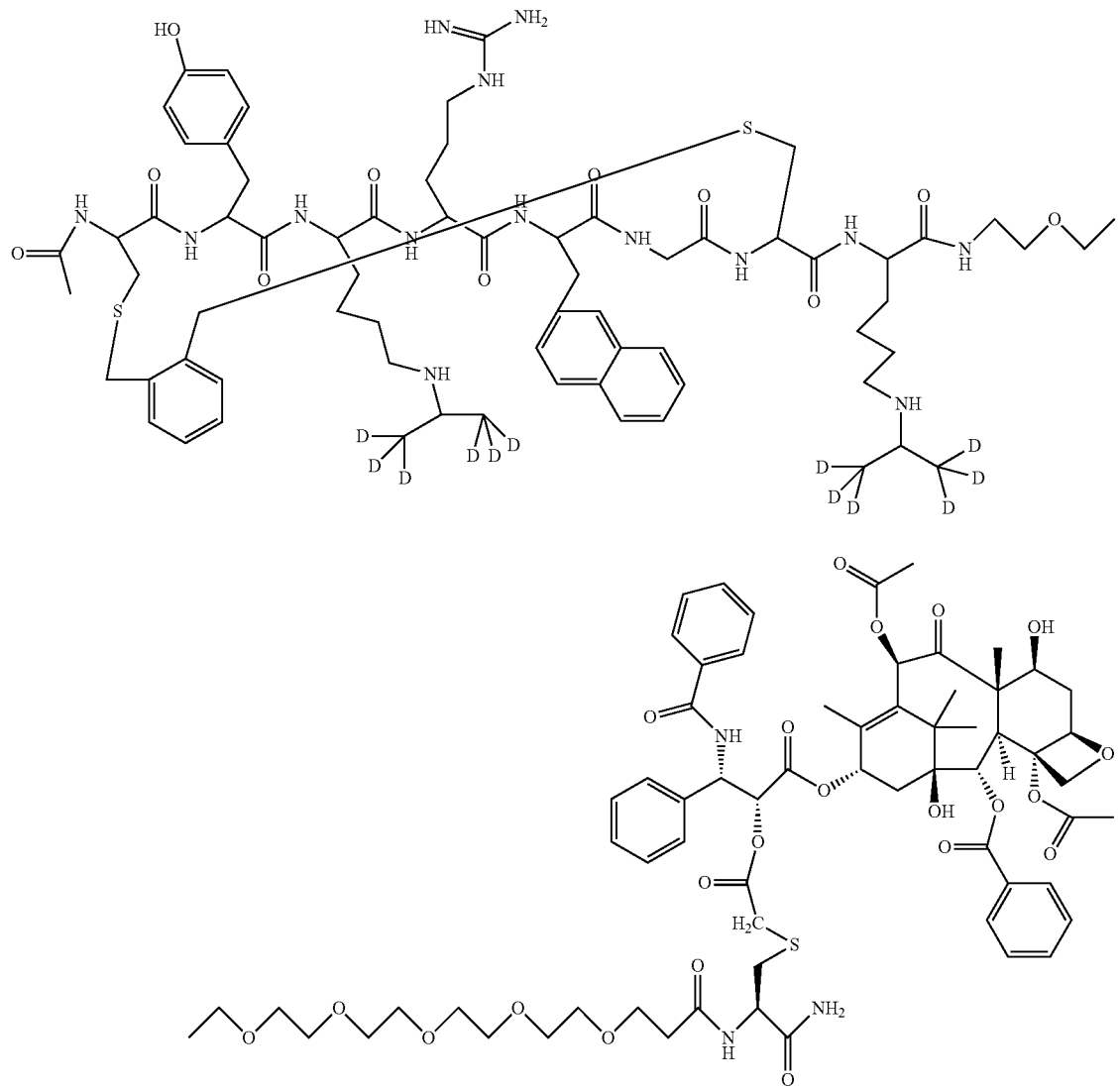

Above prepared 452 mg of 2'-bromoacetyl-paclitaxel and 905 mg of cyclized CXCR4 peptide were dissolved in 100 mL of MeCN/water (1:1, v/v). The solution was adjusted to pH 7~7.5 using 0.5M of ammonium bicarbonate. The conjugation reaction was completed in about half an hour as confirmed by MS at room temperature. The final product was purified using a reverse-phased preparative column Daisogel (50×250 mm, 8 μm); mobile phases—Solvent A: 0.1% TFA water; Solvent B: 0.1% TFA acetonitrile. Fractions containing the target product MB1707-D12 were combined and lyophilized (a TFA salt). Salt exchange as described above afforded a peptide in acetate salt. Analytical HPLC purity of the final peptide product is 99.01%; MW cal.: 2626.20 Da; MW obs.: 2623.35 Da.

Example 3. Synthesis of Cyclic[Ac-HCys-Tyr-Lys(iPr)-d-Ar-2Nal-Gly-Cys]-Lys(iPr)-PEG$_6$-COOH, a Disulfide Ring hCys1-Cys7

(SEQ ID NO: 10)

The sequence hCys(Trt)-Tyr(tBu)-Lys(iPr, Boc)-(D-Arg(Pbf))-2Nal-Gly-Cys(Trt)-Lys(iPr, Boc)-PEG6 (SEQ ID NO:11) was assembled by standard Fmoc chemistry using 2-chlorotrityl chloride resin. Briefly, 4.0 grams of the resin was swollen in DCM for 2 h, washed four times with DMF and then once with DCM. The loading of the first residue Fmoc-PEG6 was carried out in DCM using four equivalents of amino acid activated with five equivalents of DIEA. The coupling at room temperature for 1.5 h was followed by capping of the unreacted substitution sites with methanol/DIEA (1:1, v/v, 24 mL) for 30 min. Removal of Fmoc protection was carried out in 20% piperidine in DMF for 20 min at room temperature and washed several times with DMF. Ninhydrin test was negative. Stepwise chain assembly of the linear peptide using standard Fmoc chemistry was continued consequentially through a cycle of deprotection, activation and coupling.

After the coupling of last residue Fmoc-hCys(Trt)-OH, Fmoc protection was removed again using 20% piperidine in DMF for 20 min. N-terminal acetylation was carried out with 5 mL of a mixture of acetic anhydride/DIEA/DMF (1:1:4, v/v/v) for 30 min at room temperature. The resin was then washed with DMF three time and then with DCM twice, dried under vacuum.

The crude linear peptide cleavage and side chain protections were carried out using 10 mL of a cleavage cocktail of TFA/EDT/TIS/H$_2$O/thioanisole/phenol per gram of crude peptide resin (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. Then to the cleavage mixture was added eight volumes of methyl t-butyl ether. The crude peptide precipitates were separated by centrifugation at 3000 r pm for 3 min. The crude peptide Compound C

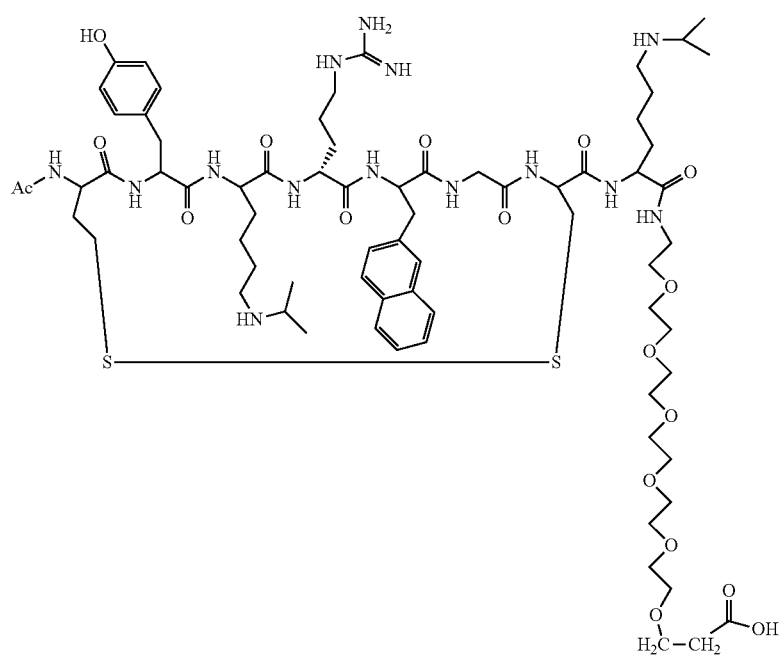

precipitates were washed three times with methyl t-butyl ether. The crude peptide was then dissolved in an aqueous acetonitrile and lyophilized.

The crude lyophilized product was used directly in the cyclization reaction. The lyophilized crude peptide was dissolved in 20% acetic acid at 0.5 mg/mL. Under stirring, add 0.03% mole/L iodine solution until the peptide solution turned light yellow. The solution was protected from visible light during the cyclization. Cyclization was completed within 0.5 h as monitored by mass spectroscopy. The cyclized final product was purified using a reverse-phased preparative column Daisogel (50×250 mm, 8 μm) with mobile phases—A: 0.1% TFA water; B: 0.1% TFA acetonitrile. Fractions containing the target product were combined and lyophilized (a TFA salt).

Example 4. Synthesis of Cyclic[Ac-hCys-Tyr-Lys(iPr)-d-Arg-2Nal-Gly-Cys]-Lys(iPr)-PEG$_6$-Lys, a Disulfide Ring hCys1-Cys7

(SEQ ID NO: 12)

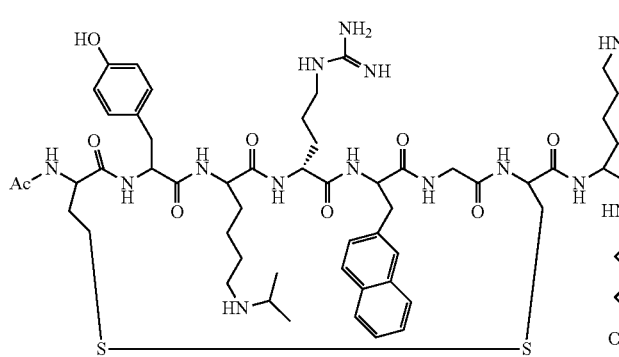
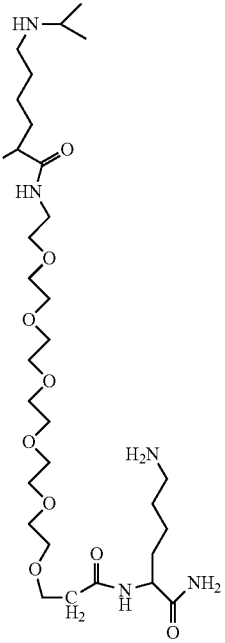

Compound D

The sequence hCys(Trt)-Tyr(tBu)-Lys(iPr,Boc)-(D-Arg(Pbf))-2Nal-Gly-Cys(Trt)-Lys(iPr,Boc)-PEG6-Lys(Boc) (SEQ ID NO:13) was assembled manually by standard Fmoc chemistry using Rink AM resin. Briefly, 3.6 grams of Rink AM resin was swollen in DCM for 14 h and then washed four times with DMF. Removal of Fmoc was carried out in 20% piperidine in DMF for 20 min at room temperature and washed several times with DMF. Ninhydrin test was negative. Stepwise chain assembly started from the C-terminal end of the linear peptide and was accomplished in nine major steps. In step 1, three equivalents of protected amino acid Fmoc-Lys(Boc) were activated with DIC/HOBt in DMF, and coupled to the Fmoc-removed Rink AM resin above for 2 h at room temperature followed by Fmoc removal using 20% piperidine in DMF for 20 min. In step 2, three equivalents of Fmoc-PEG6 acid were activated with DCC/HOBt in DMF and coupled to the deprotected resin from step 1. Appropriate steps were continued using Fmoc-protected amino acids, respectively, until the coupling of Fmoc-hCys(Trt)-OH.

After the coupling of last residue Fmoc-hCys(Trt)-OH, Fmoc protection was removed again using 20% piperidine in DMF for 20 min. N-terminal acetylation was carried out with 5 mL of a mixture of acetic anhydride/DIEA/DMF (1:1:4, v/v/v) for 30 min at room temperature. The resin was then washed with DMF three time and then with DCM twice, dried under vacuum.

The finished peptide was deprotected and cleaved from the resin using 10 mL/gram of resin of a cleavage cocktail of TFA/EDT/TIS/H$_2$O/thioanisole/phenol (per 100 mL of solution contains 81.5 mL TFA, 2.5 mL EDT, 1.0 mL TIS, 5.0 mL H$_2$O, 5.0 mL thioanisole, and 5.0 grams phenol) for 70 min at room temperature. To the cleavage mixture was added eight volumes of methyl t-butyl ether. The crude peptide precipitates were separated by centrifugation at 3000 rpm for 3 min. The crude peptide precipitates were washed three times with methyl t-butyl ether. The crude peptide was then dissolved in aqueous acetonitrile and lyophilized.

The crude lyophilized product was used directly in the cyclization reaction. The lyophilized crude peptide was dissolved in water containing 20% acetic acid at 0.5 mg/mL (500 mg of crude peptide in one liter). Under stirring, 0.03% mole/L iodine solution was added to the peptide solution until the solution became pale yellow. Cyclization was complete within 0.5 h in dark as monitored by mass spectroscopy. The cyclized final product was purified using a reverse-phased preparative column Daisogel (50×250 mm, 8 μm); mobile phases—Solvent A: 0.1% TFA water; Solvent B: 0.1% TFA acetonitrile. Fractions containing the target product were combined and lyophilized (a TFA salt).

Example 5. Cyclic[Acetyl-hCys-Tyr-Lys(iPr)-d-Arg-2Nal-Gly-Cys]-Lys(iPr)-mini-PEG$_6$-Cys-Amide, a Disulfide Ring hCys1-Cys7

(SEQ ID NO: 14)

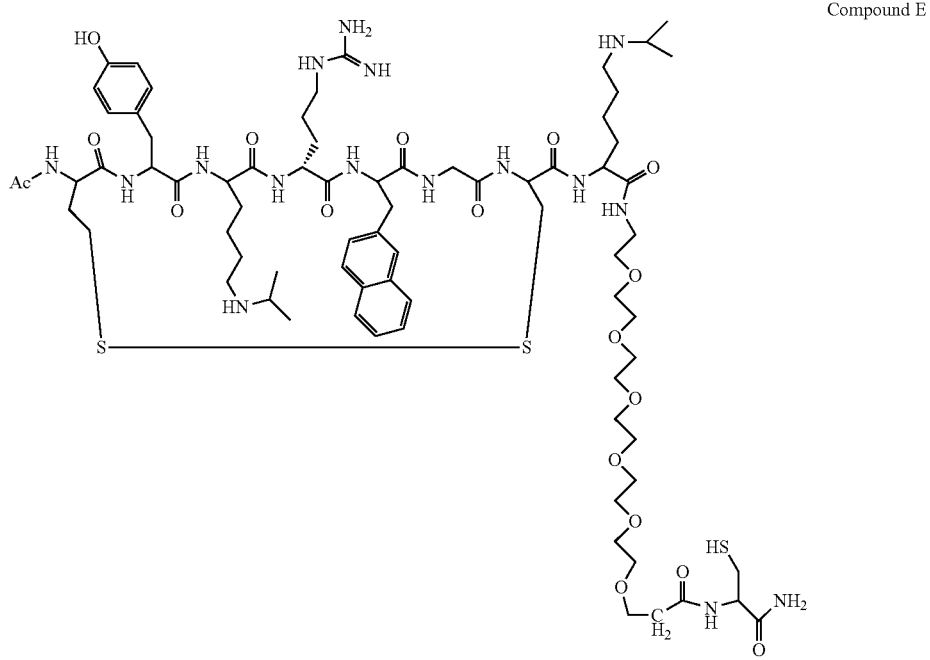

Compound E

The sequence hCys(Mmt)-Tyr(tBu)-Lys(iPr,Boc)-(D-Arg(Pbf))-2Nal-Gly-Cys(Mmt)-Lys(iPr,Boc)-PEG6-Cys(Trt) (SEQ ID NO:15) was assembled by standard Fmoc chemistry using Sieber amide AM resin (Xi'an LanXiao Chemical Limited, Xi'an, China). Briefly, 4 g of Sieber amide AM resin was swollen in 30 mL of DCM for 2 h and then washed four times with DMF. Removal of Fmoc was carried out in 25 mL of 20% piperidine in DMF for 20 min at room temperature and washed several times with DMF. Ninhydrin test was negative. Stepwise chain assembly started with Fmoc-Cys(Trt)-OH from the C-terminal end of the linear peptide. Three equivalents of protected amino acid Fmoc-Cys(Trt)-OH were activated with DIC/HOBt in 8 mL of DMF, and coupled to the Fmoc-removed Sieber amide AM resin prepared above for 2 h at room temperature. Ninhydrin test was negative. Capping of the non-reacted amino group was performed for 30 min with 16 mL of a mixture of acetic anhydride/DIEA/DCM at a volume ratio of 1:1:4. This was followed by Fmoc removal using 25 mL of 20% piperidine in DMF for 20 min. The following residues were coupled sequentially without capping: Fmoc-(mini-PEG6)-OH, Fmoc-Lys(iPr,Boc)-OH, Fmoc-Cys(Mmt)-OH, Fmoc-Gly-OH, Fmoc-2Nal-OH, Fmoc-D-Arg(Pbf))-OH, Fmoc-Lys(iPr,Boc)-OH, Fmoc-Tyr(tBu)-OH, and Fmoc-hCys(Mmt)-OH. After the coupling of last residue Fmoc-hCys(Mmt), Fmoc protection was removed again using 25 mL of 20% piperidine in DMF for 20 min. N-terminal acetylation was carried out with 16 mL of a mixture of acetic anhydride/DIEA/DMF (1:1:4, v/v/v) for 30 min at room temperature. The resin was then washed with 25 mL of DMF three time and then with 25 mL of DCM three times, then dried under vacuum to afford 8 grams of peptide resin containing the assembled target linear peptide. The dried resin was used in the following operation.

Removal of Mmt protection on Cys residues and Cleavage of partial protected linear peptide from peptide resin: About 2 grams of above peptide resin was swelled in 30 mL of DCM for 30 min. Total 100 mL of a cleavage/deprotection cocktail (TFA/H$_2$O/EDT/TIS/DCM, 6:3:1.5:3:86.5, v/v) was added to above swelled resin to remove Mmt protection of Cys side chain. The mixture was stirred for 20 min at room temperature. This deprotection and cleavage procedure was repeated once using another 100 mL of the cleavage/deprotection cocktail above at room temperature for 20 min. After removal of the solid resin by filtration, the cleavage solutions containing the partially deprotected linear peptide were combined and concentrated under vacuum using a rotary evaporator. The residues (crude peptide) were then lyophilized to afford about 1 gram of partially deprotected crude linear peptide.

The crude lyophilized product was used directly in the cyclization reaction. The lyophilized crude peptide was dissolved in water containing 20% acetic acid at 0.5 mg/mL (500 mg of crude peptide in one liter). Under stirring, 0.03% mole/L iodine solution was added to the peptide solution until the solution became pale yellow. Cyclization was complete within 0.5 h in dark as monitored by mass spectroscopy. The cyclization reaction was allowed to proceed for 1 h at room temperature. The reaction mixture was then divided into several equal portions and lyophilized.

Side chain deprotection of the cyclized peptide: The lyophilized crude cyclized peptide was deprotected using a cleavage cocktail (TFA/EDT/TIS/H$_2$O/thioanisole/phenol, per 100 mL of solution contains 81.5 mL TFA, 2.5 mL EDT, 1.5 mL TIS, 5.0 mL H$_2$O, 5.0 mL thioanisole, and 5.0 grams phenol) at 10 mL each container, for 60 min. To the cleavage mixture was added 4 volumes of cold ethyl ether. The crude peptide precipitates were separated by centrifugation at 3000 rpm for 2 min. The crude peptide precipitates were washed three times with ethyl ether. The crude peptide was purified to a purity>90% on preparative HPLC, and lyophilized.

Example 6. Preparation of PDC-CXCR4 Peptide Conjugate Compound F (SEQ ID NO: 16)

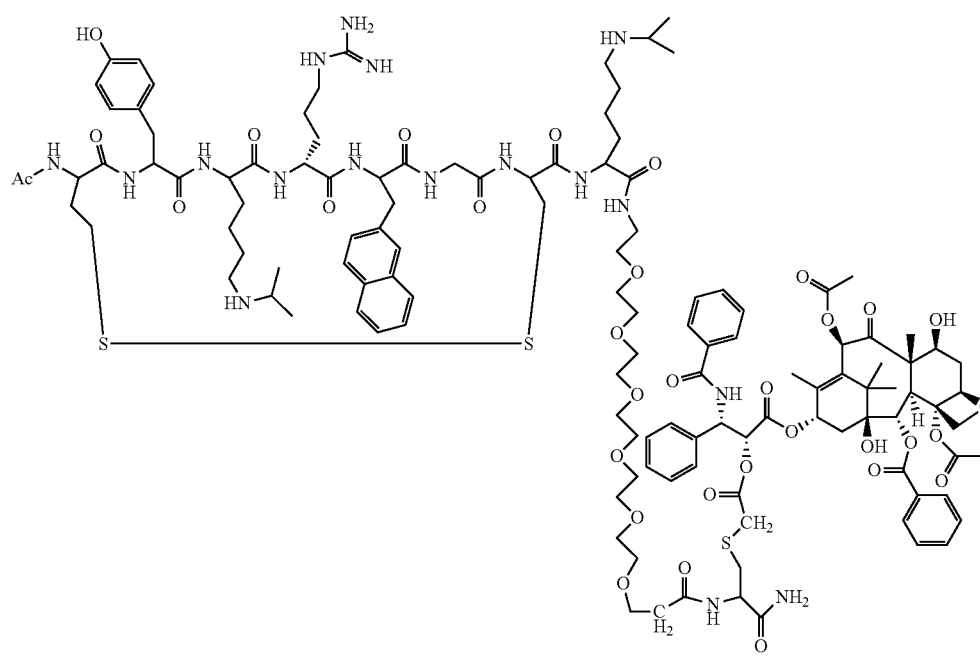

Compound F

Above prepared 450 mg of 2'-bromoacetyl-paclitaxel and 905 mg of cyclized CXCR4 peptide Compound C are dissolved in 100 mL of MeCN/water (1:1, v/v). The solution is adjusted to pH 7~7.5 using 0.5M of ammonium bicarbonate. The conjugation reaction is monitored by MS and the reaction completed in about half an hour. The final product is purified using a reverse-phased preparative column Daisogel (50×250 mm, 8 μm); mobile phases—Solvent A: 0.1% TFA water; Solvent B: 0.1% TFA acetonitrile. Fractions containing the target product Compound F are combined and lyophilized (a TFA salt). Salt exchange as described above affords a peptide in acetate salt.

Example 7. Preparation of Compounds G-P

Compounds G-P are prepared in a similar fashion starting with a Rink amide resin or 2-chlorotrityl resin or a Sieber amide AM resin using standard Fmoc solid phase peptide chemistry.

(SEQ ID NO: 17)

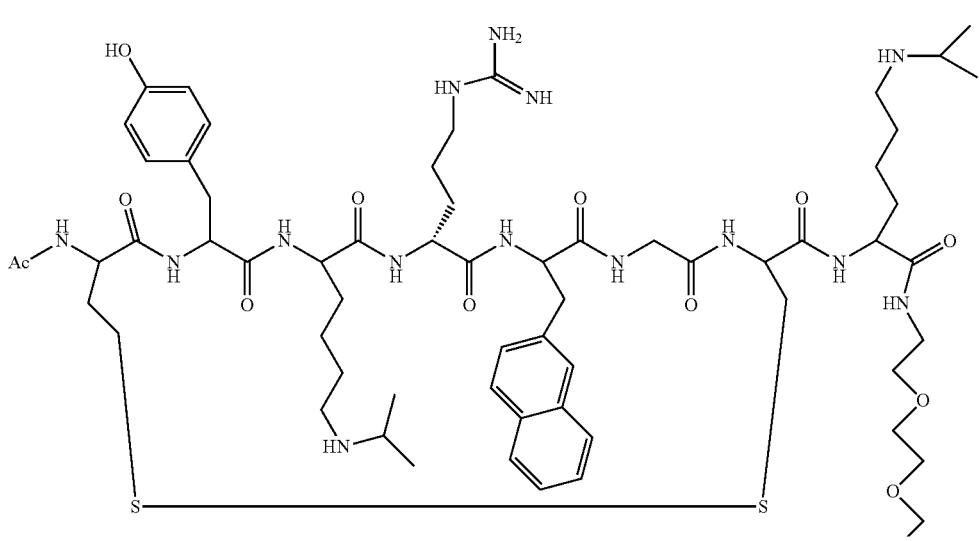

Compound G

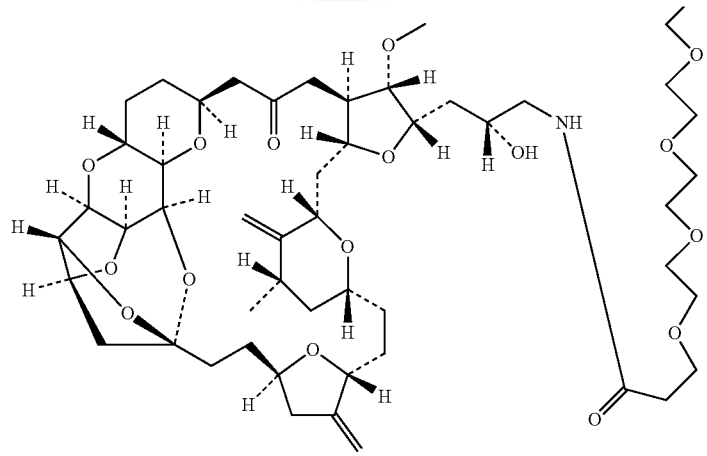
Molecular Weight: 2239.80; m/z: 2239.19 (100.0%)
(SEQ ID NO: 18)
Compound H
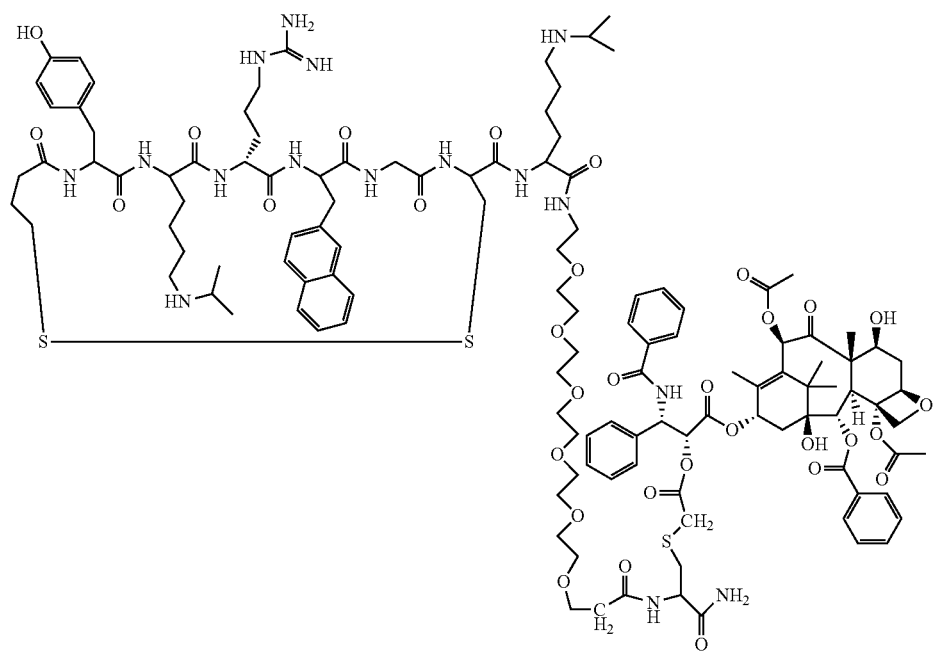

(SEQ ID NO: 19)
Compound I
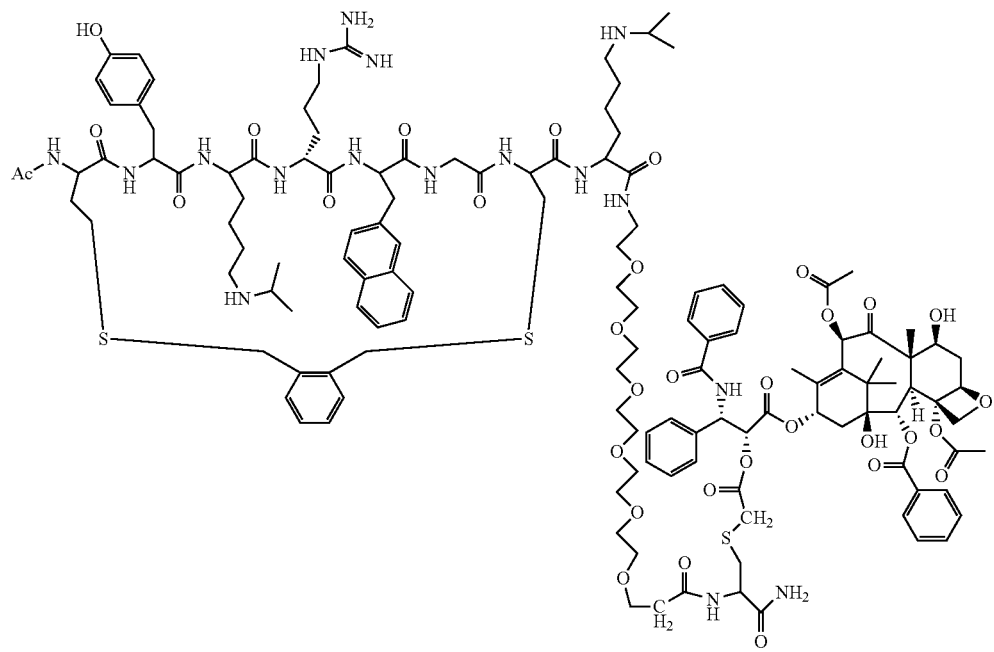
(SEQ ID NO: 20)
Compound J
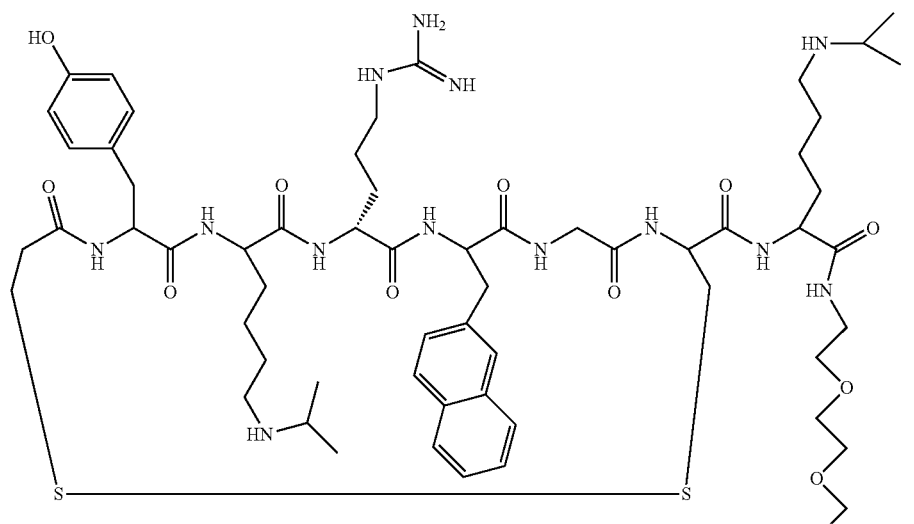

-continued
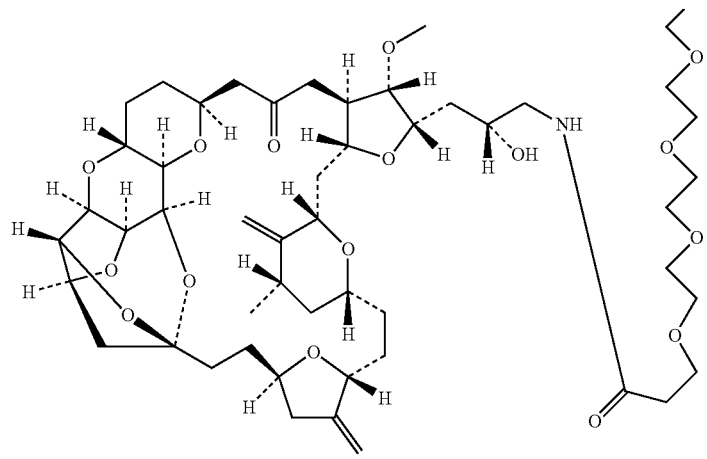
(SEQ ID NO: 21)
Compound K
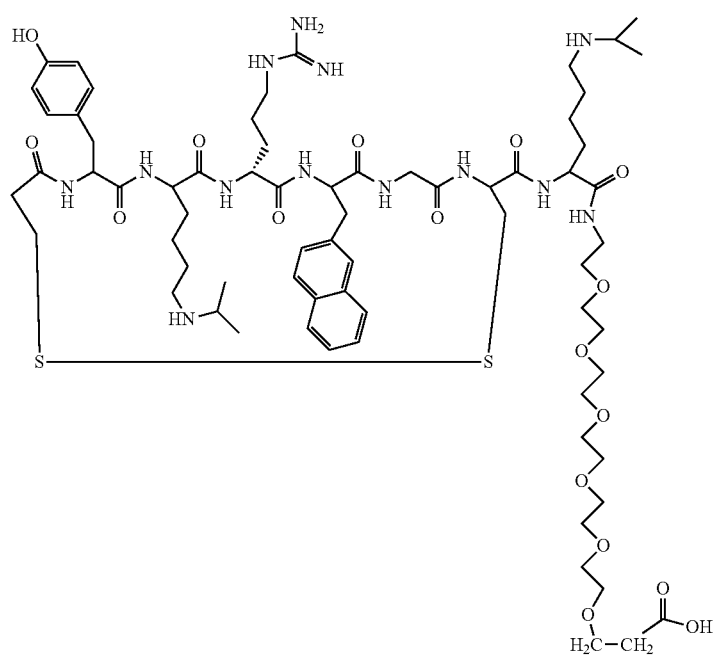

(SEQ ID NO: 22)
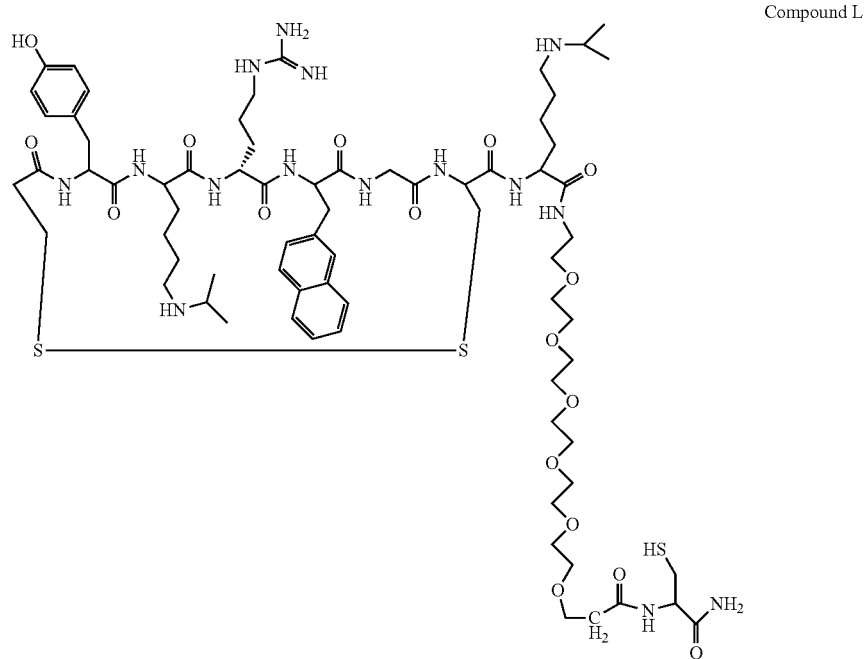
Compound L
(SEQ ID NO: 23)
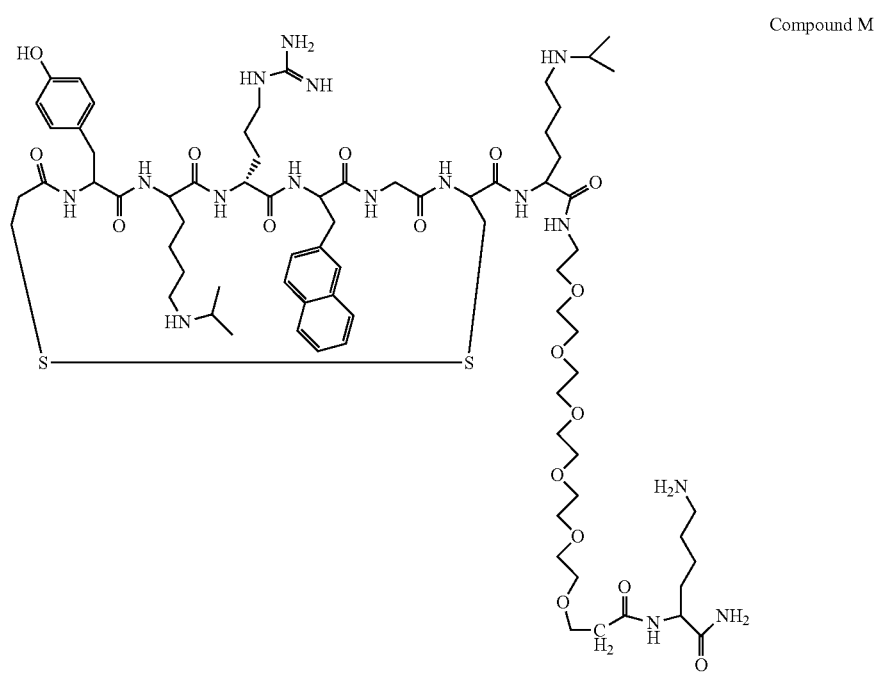
Compound M (SEQ ID NO: 24)
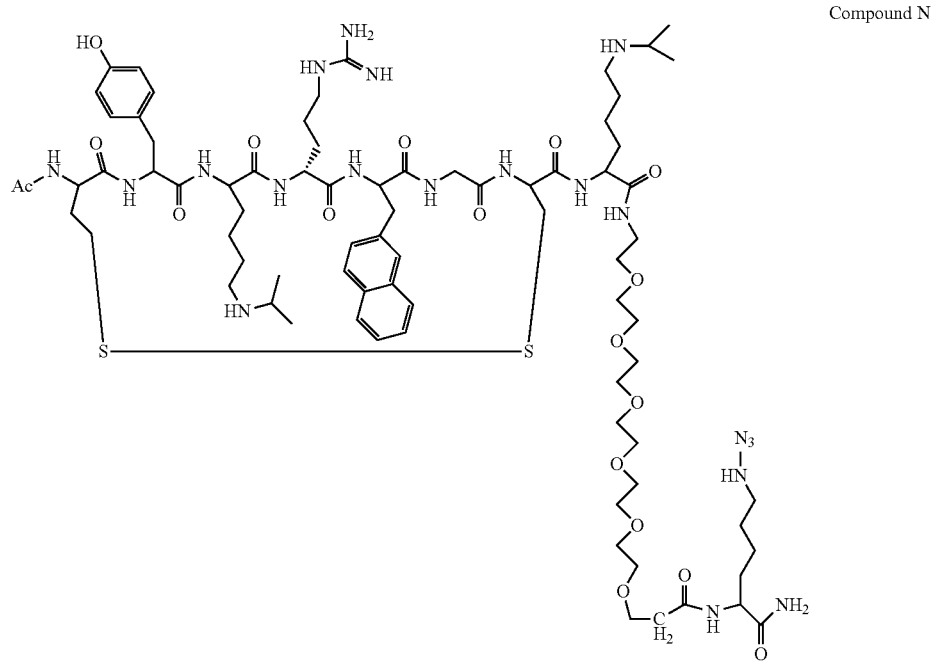
Compound N
(SEQ ID NO: 25)
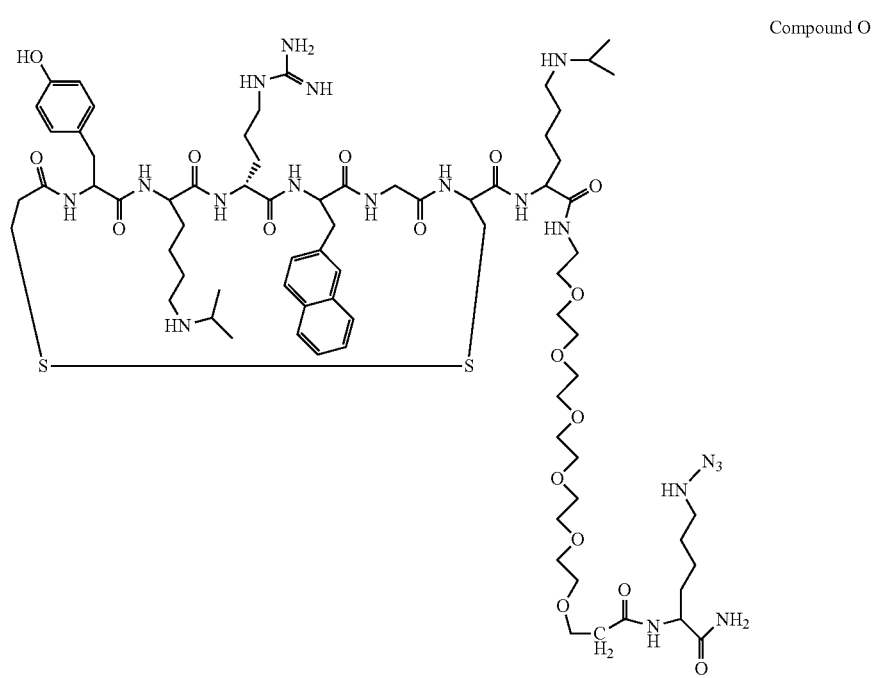
Compound O (SEQ ID NO: 26)

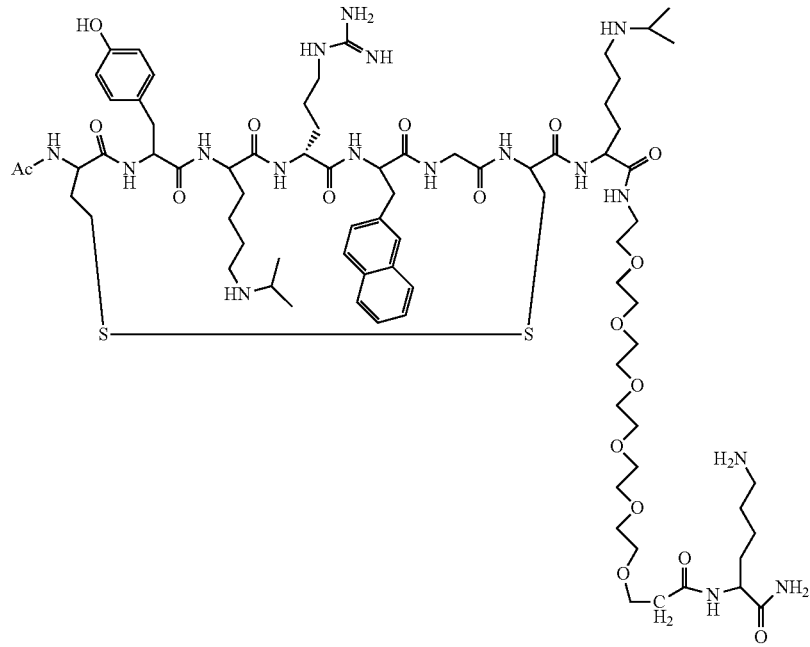

Compound P

Example 8. Synthesis of Isotopically Labelled Compounds

Using the procedures described in Examples above and using a corresponding deuterated compound B-D12 or a corresponding tritium labelled compound (i.e., compound B-T12, for tritium labelled compound of B, similar to B-D12 but where deuterium are replaced with tritium) deuterated or tritium labelled cyclic peptide moieties are prepared. Use of these deuterium labelled (B-D12) and tritium labelled (B-T12) compounds provide synthesis of corresponding deuterium labelled ("-D12") and tritium labelled (i.e., "-T12") compounds A-P, i.e., compounds A-D12, A-T12, B-D12, B-T12, C-D12, C-T12, . . . P-D12, and P-T12.

Human CXCR4/$^{125}$I-SDF-1α Binding Inhibition Assay: (Performed by EUROFINS CEREP SA, Le Bois l'Eveque, 86600 Celle L'Evescault, France): Human chemokine receptor CXCR4 expressed in Chem-1 cells were used in modified HEPES buffer pH 7.4. A 0.5 μg (Membrane protein may change from lot to lot, the concentration used will be adjusted if necessary), aliquot was incubated with 0.03 nM [$^{125}$I]SDF-1α for 90 minutes at 25° C. Non-specific binding was estimated in the presence of 30 nM SDF-1a. Membranes were filtered and washed, filters were then counted to determine [$^{125}$I]SDF-1α specifically bound. Compounds were screened starting at 10 μM with 11-point dilutions (Valenzuela-Fernandez A, et al. *J Biol Chem.* 277(18): 15677, 2002). The CXCR4 binding affinity of the antagonist peptides disclosed herein and their drug-conjugates is 1.0 μM or less to be practical for therapeutic use.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

SEQUENCE LISTING

```
<160> NUMBER OF SEQ ID NOS: 26

<210> SEQ ID NO 1
<211> LENGTH: 8
<212> TYPE: PRT
<213> ORGANISM: Artificial Sequence
<220> FEATURE:
<223> OTHER INFORMATION: Compound of Formula I
<220> FEATURE:
<221> NAME/KEY: MISC_FEATURE
```

```
<222> LOCATION: (1)..(1)
<223> OTHER INFORMATION: along with the sulfur atom that is attached
      thereto is 3-mercaptopropionic acid, optionally substituted
      cysteine, optionally substituted homocysteine, or optionally
      substituted penicillamine
<220> FEATURE:
<221> NAME/KEY: MISC_FEATURE
<222> LOCATION: (1)..(7)
<223> OTHER INFORMATION: Forms cyclic structure via sulfur atoms and a
      linker -(CH2-Ar1-CH2)a-, where Ar1 is an optionally substituted
      aryl and a is 0 or 1
<220> FEATURE:
<221> NAME/KEY: MISC_FEATURE
<222> LOCATION: (3)..(3)
<223> OTHER INFORMATION: Arg, Dap, Dab, Orn, Lys, Dap(iPr), Dab(iPr),
      Orn(iPr), or Lys(iPr);mine, each of which can be (L)- or
      (D)-isomer
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: along with the sulfur atom that is attached
      thereto is cysteine or homocysteine
<220> FEATURE:
<221> NAME/KEY: MISC_FEATURE
<222> LOCATION: (8)..(8)
<223> OTHER INFORMATION: can be 1 to 4 amino acid each of which can be
      independently Gly, Phe, 2Nal, 1Nal, Arg, Dap, Dab, Orn, Lys,
      Dap(iPr), Dab(iPr), Orn(iPr), Lys(iPr), and each of which can be
      independently (L)- or (D)-isomer.

<400> SEQUENCE: 1

Xaa Tyr Xaa Arg Xaa Gly Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Compound of Formula IA
<220> FEATURE:
<221> NAME/KEY: MISC_FEATURE
<222> LOCATION: (1)..(1)
<223> OTHER INFORMATION: along with the sulfur atom that is attached
      thereto is 3-mercaptopropionic acid, optionally substituted
      cysteine, optionally substituted homocysteine, or optionally
      substituted penicillamine
<220> FEATURE:
<221> NAME/KEY: MISC_FEATURE
<222> LOCATION: (1)..(7)
<223> OTHER INFORMATION: Forms cyclic structure via sulfur atoms and a
      linker -(CH2-Ar1-CH2)a-, where Ar1 is an optionally substituted
      aryl and a is 0 or 1
<220> FEATURE:
<221> NAME/KEY: MISC_FEATURE
<222> LOCATION: (3)..(3)
<223> OTHER INFORMATION: Arg, Dap, Dab, Orn, Lys, Dap(iPr), Dab(iPr),
      Orn(iPr), or Lys(iPr);mine, each of which can be (L)- or
      (D)-isomer
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
```

```
<222> LOCATION: (7)..(7)
<223> OTHER INFORMATION: along with the sulfur atom that is attached
      thereto is cysteine or homocysteine
<220> FEATURE:
<221> NAME/KEY: MISC_FEATURE
<222> LOCATION: (8)..(8)
<223> OTHER INFORMATION: can be 1 to 4 amino acid each of which can be
      independently Gly, Phe, 2Nal, 1Nal, Arg, Dap, Dab, Orn, Lys,
      Dap(iPr), Dab(iPr), Orn(iPr), Lys(iPr), and each of which can be
      independently (L)- or (D)-isomer
<220> FEATURE:
<221> NAME/KEY: MISC_FEATURE
<222> LOCATION: (8)..(8)
<223> OTHER INFORMATION: one of the amino acid is attached to -L1-Q
      moiety

<400> SEQUENCE: 2

Xaa Tyr Xaa Arg Xaa Gly Xaa Xaa
1               5

<210> SEQ ID NO 3
<211> LENGTH: 14
<212> TYPE: PRT
<213> ORGANISM: Artificial Sequence
<220> FEATURE:
<223> OTHER INFORMATION: Compound of Formula 1A
<220> FEATURE:
<221> NAME/KEY: MISC_FEATURE
<222> LOCATION: (1)..(1)
<223> OTHER INFORMATION: along with the sulfur atom that is attached
      thereto is 3-mercaptopropionic acid, optionally substituted
      cysteine, optionally substituted homocysteine, or optionally
      substituted penicillamine
<220> FEATURE:
<221> NAME/KEY: MISC_FEATURE
<222> LOCATION: (1)..(7)
<223> OTHER INFORMATION: Forms cyclic structure via sulfur atoms and a
      linker -(CH2-Ar1-CH2)a-, where Ar1 is an optionally substituted
      aryl and a is 0 or 1
<220> FEATURE:
<221> NAME/KEY: MISC_FEATURE
<222> LOCATION: (3)..(3)
<223> OTHER INFORMATION: Arg, Dap, Dab, Orn, Lys, Dap(iPr), Dab(iPr),
      Orn(iPr), or Lys(iPr);mine, each of which can be (L)- or
      (D)-isomer
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: along with the sulfur atom that is attached
      thereto is cysteine or homocysteine
<220> FEATURE:
<221> NAME/KEY: MISC_FEATURE
<222> LOCATION: (8)..(8)
<223> OTHER INFORMATION: can be 1 to 4 amino acid each of which can be
      independently Gly, Phe, 2Nal, 1Nal, Arg, Dap, Dab, Orn, Lys,
      Dap(iPr), Dab(iPr), Orn(iPr), Lys(iPr), and each of which can be
      independently (L)- or (D)-isomer.
<220> FEATURE:
<221> NAME/KEY: MISC_FEATURE
<222> LOCATION: (9)..(9)
<223> OTHER INFORMATION: L1a which is a polymeric linker having a
      functional group for linking Q, wherein L1
      comprises from about 2 to about 20 monomers or copolymers;
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
```

```
<222> LOCATION: (11)..(11)
<223> OTHER INFORMATION: is Y1 which is a side-chain function group of
      amino acid AA4
<220> FEATURE:
<221> NAME/KEY: MISC_FEATURE
<222> LOCATION: (12)..(12)
<223> OTHER INFORMATION: is L2 which is a non-polymeric linker
<220> FEATURE:
<221> NAME/KEY: MISC_FEATURE
<222> LOCATION: (13)..(13)
<223> OTHER INFORMATION: is Y2 which is a functional group of said
      medically useful compound or a functional group of L2;
<220> FEATURE:
<221> NAME/KEY: MISC_FEATURE
<222> LOCATION: (14)..(14)
<223> OTHER INFORMATION: is Z which is a medically useful compound

<400> SEQUENCE: 3

Xaa Tyr Xaa Arg Xaa Gly Xaa Xaa Xaa Xaa Xaa Xaa Xaa Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Compound A
<220> FEATURE:
<221> NAME/KEY: MISC_FEATURE
<222> LOCATION: (1)..(1)
<223> OTHER INFORMATION: Acetylated on the alpha-amino group
<220> FEATURE:
<221> NAME/KEY: MISC_FEATURE
<222> LOCATION: (1)..(7)
<223> OTHER INFORMATION: Forms cyclic structure via sulfur atoms and a
      linker -CH2-Phenyl-CH2-
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amine bond with Lys and an amide
      bond with alpha-amino group of cysteine
<220> FEATURE:
<221> NAME/KEY: MISC_FEATURE
<222> LOCATION: (10)..(10)
<223> OTHER INFORMATION: thiol functional group of cysteine attached to
      paclitaxel via -CH2-C(=O)- linker

<400> SEQUENCE: 4

Cys Tyr Lys Arg Xaa Gly Cys Lys Xaa Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Sieber Amide AM Resin bound Peptide of Exaple 1
<220> FEATURE:
```

```
<221> NAME/KEY: MISC_FEATURE
<222> LOCATION: (1)..(1)
<223> OTHER INFORMATION: Fmoc and Mmt protected
<220> FEATURE:
<221> NAME/KEY: MISC_FEATURE
<222> LOCATION: (2)..(2)
<223> OTHER INFORMATION: tBu protected
<220> FEATURE:
<221> NAME/KEY: MISC_FEATURE
<222> LOCATION: (3)..(3)
<223> OTHER INFORMATION: side chain amino group is substituted with iPr
      and Boc
<220> FEATURE:
<221> NAME/KEY: MISC_FEATURE
<222> LOCATION: (4)..(4)
<223> OTHER INFORMATION: Pbf protected (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: Mmt protected
<220> FEATURE:
<221> NAME/KEY: MISC_FEATURE
<222> LOCATION: (8)..(8)
<223> OTHER INFORMATION: side chain amino group is substituted with iPr
      and Boc
<220> FEATURE:
<221> NAME/KEY: MISC_FEATURE
<222> LOCATION: (9)..(9)
<223> OTHER INFORMATION: mini-PEG6 linker
<220> FEATURE:
<221> NAME/KEY: MISC_FEATURE
<222> LOCATION: (10)..(10)
<223> OTHER INFORMATION: Trt protected and linked to Sieber Amide AM
      Resin

<400> SEQUENCE: 5

Cys Tyr Lys Arg Xaa Gly Cys Lys Xaa Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Compound B
<220> FEATURE:
<221> NAME/KEY: MISC_FEATURE
<222> LOCATION: (1)..(1)
<223> OTHER INFORMATION: alpha-amino group is acetylated
<220> FEATURE:
<221> NAME/KEY: MISC_FEATURE
<222> LOCATION: (1)..(7)
<223> OTHER INFORMATION: Forms cyclic structure via sulfur atoms and a
      linker -CH2-Phenyl-CH2-
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
```

-continued

<223> OTHER INFORMATION: a PEG-7 linker with modified functional groups
    on both terminal ends to form an amine bond with Lys and an amide
    bond with alpha-amino group of cysteine

<400> SEQUENCE: 6

Cys Tyr Lys Arg Xaa Gly Cys Lys Xaa Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Peptide Chain Example 2 linked to Sieber Amide
    AM Resin
<220> FEATURE:
<221> NAME/KEY: MISC_FEATURE
<222> LOCATION: (1)..(1)
<223> OTHER INFORMATION: Fmoc and Mmt protected
<220> FEATURE:
<221> NAME/KEY: MISC_FEATURE
<222> LOCATION: (2)..(2)
<223> OTHER INFORMATION: tBu protected
<220> FEATURE:
<221> NAME/KEY: MISC_FEATURE
<222> LOCATION: (3)..(3)
<223> OTHER INFORMATION: Boc protected
<220> FEATURE:
<221> NAME/KEY: MISC_FEATURE
<222> LOCATION: (4)..(4)
<223> OTHER INFORMATION: Pbf protected (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: Mmt protected
<220> FEATURE:
<221> NAME/KEY: MISC_FEATURE
<222> LOCATION: (8)..(8)
<223> OTHER INFORMATION: Boc protected
<220> FEATURE:
<221> NAME/KEY: MISC_FEATURE
<222> LOCATION: (9)..(9)
<223> OTHER INFORMATION: mini-PEG6 linker
<220> FEATURE:
<221> NAME/KEY: MISC_FEATURE
<222> LOCATION: (10)..(10)
<223> OTHER INFORMATION: Trt portected and linked to Sieber Amide AM
    Resin

<400> SEQUENCE: 7

Cys Tyr Lys Arg Xaa Gly Cys Lys Xaa Cys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Compound B-D12 (Deuterated)
<220> FEATURE:
<221> NAME/KEY: MISC_FEATURE
<222> LOCATION: (1)..(1)
<223> OTHER INFORMATION: alpha-amino group is acetylated
<220> FEATURE:
<221> NAME/KEY: MISC_FEATURE
<222> LOCATION: (1)..(7)
<223> OTHER INFORMATION: Forms cyclic structure via sulfur atoms and a
    linker -CH2-Phenyl-CH2-
<220> FEATURE:
<221> NAME/KEY: MISC_FEATURE
<222> LOCATION: (3)..(3)

```
<223> OTHER INFORMATION: substituted with deutereated iPr on the
      side-chain amino group
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: substituted with deuterated iPr group on the
      side-chain amino group
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amine bond with Lys and an amide
      bond with alpha-amino group of cysteine

<400> SEQUENCE: 8

Cys Tyr Lys Arg Xaa Gly Cys Lys Xaa Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Compound A-D12 (Deuterated Compound A)
<220> FEATURE:
<221> NAME/KEY: MISC_FEATURE
<222> LOCATION: (1)..(1)
<223> OTHER INFORMATION: acetylated on the alpha-amino group
<220> FEATURE:
<221> NAME/KEY: MISC_FEATURE
<222> LOCATION: (1)..(7)
<223> OTHER INFORMATION: Forms cyclic structure via sulfur atoms and a
      linker -CH2-Phenyl-CH2-
<220> FEATURE:
<221> NAME/KEY: MISC_FEATURE
<222> LOCATION: (3)..(3)
<223> OTHER INFORMATION: substituted with deuterated iPr group on the
      side chain amino functional group
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: substituted with deuterated iPr group on the
      side chain amino functional group
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amine bond with Lys and an amide
      bond with alpha amino group of cysteine
<220> FEATURE:
<221> NAME/KEY: MISC_FEATURE
<222> LOCATION: (10)..(10)
<223> OTHER INFORMATION: thiol functional group of cysteine attached to
      paclitaxel via -CH2-C(=O)- linker

<400> SEQUENCE: 9

Cys Tyr Lys Arg Xaa Gly Cys Lys Xaa Cys
1               5                   10
```

```
<210> SEQ ID NO 10
<211> LENGTH: 8
<212> TYPE: PRT
<213> ORGANISM: Artificial Sequence
<220> FEATURE:
<223> OTHER INFORMATION: Compound C in Example 3
<220> FEATURE:
<221> NAME/KEY: MISC_FEATURE
<222> LOCATION: (1)..(1)
<223> OTHER INFORMATION: acetylated on the alpha-amino group
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: substituted with iPr group on the side chain
      amino functional group
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: substituted wth iPr group on the side chain
      amino functional group
<220> FEATURE:
<221> NAME/KEY: MISC_FEATURE
<222> LOCATION: (8)..(8)
<223> OTHER INFORMATION: substituted with a PEG-6 linker with modified
      functional groups on both terminal ends to form an amide bond with
      the carboxy terminal of Lys and terminated -CH2-CH2-CO2H group on
      the other end

<400> SEQUENCE: 10

Cys Tyr Lys Arg Xaa Gly Cys Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Protein 11 hCys Analog
<220> FEATURE:
<221> NAME/KEY: MISC_FEATURE
<222> LOCATION: (1)..(1)
<223> OTHER INFORMATION: Trt protected homocysteine
<220> FEATURE:
<221> NAME/KEY: MISC_FEATURE
<222> LOCATION: (2)..(2)
<223> OTHER INFORMATION: tBu protected
<220> FEATURE:
<221> NAME/KEY: MISC_FEATURE
<222> LOCATION: (3)..(3)
<223> OTHER INFORMATION: side chain amino group substituted with iPr and
      Boc
<220> FEATURE:
<221> NAME/KEY: MISC_FEATURE
<222> LOCATION: (4)..(4)
<223> OTHER INFORMATION: (D)-isomer that is protected with Pbf
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: Trt protected
<220> FEATURE:
```

-continued

<221> NAME/KEY: MISC_FEATURE
<222> LOCATION: (8)..(8)
<223> OTHER INFORMATION: side chain amino group is substituted with iPr
      and Boc
<220> FEATURE:
<221> NAME/KEY: MISC_FEATURE
<222> LOCATION: (8)..(8)
<223> OTHER INFORMATION: amide linked to PEG6 polymer

<400> SEQUENCE: 11

Xaa Tyr Lys Arg Xaa Gly Cys Lys
1               5

<210> SEQ ID NO 12
<211> LENGTH: 10
<212> TYPE: PRT
<213> ORGANISM: Artificial Sequence
<220> FEATURE:
<223> OTHER INFORMATION: Compound D (Protein 12)
<220> FEATURE:
<221> NAME/KEY: MISC_FEATURE
<222> LOCATION: (1)..(1)
<223> OTHER INFORMATION: homocysteine that is acetylated on the alpha-
      amino group
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substittued with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of cysteine

<400> SEQUENCE: 12

Xaa Tyr Lys Arg Xaa Gly Cys Lys Xaa Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: homocystein analog starting material
<220> FEATURE:
<221> NAME/KEY: MISC_FEATURE
<222> LOCATION: (1)..(1)
<223> OTHER INFORMATION: homocysteine that is Trt protected
<220> FEATURE:
<221> NAME/KEY: MISC_FEATURE
<222> LOCATION: (2)..(2)
<223> OTHER INFORMATION: tBu protected
<220> FEATURE:
<221> NAME/KEY: MISC_FEATURE
<222> LOCATION: (3)..(3)
<223> OTHER INFORMATION: side chain amino group is substituted with iPr
      and Boc

```
<220> FEATURE:
<221> NAME/KEY: MISC_FEATURE
<222> LOCATION: (4)..(4)
<223> OTHER INFORMATION: (D)-isomer that is protected with Pbf
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: Trt protected
<220> FEATURE:
<221> NAME/KEY: MISC_FEATURE
<222> LOCATION: (8)..(8)
<223> OTHER INFORMATION: side chain amino group is substituted with iPr
      and Boc
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of terminal Lys
<220> FEATURE:
<221> NAME/KEY: MISC_FEATURE
<222> LOCATION: (10)..(10)
<223> OTHER INFORMATION: Boc protected

<400> SEQUENCE: 13

Xaa Tyr Lys Arg Xaa Gly Cys Lys Xaa Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Compound E (Peptide 14)
<220> FEATURE:
<221> NAME/KEY: MISC_FEATURE
<222> LOCATION: (1)..(1)
<223> OTHER INFORMATION: hohomocysteine that is acetylated on the alpha-
      amino group
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of cysteine

<400> SEQUENCE: 14

Xaa Tyr Lys Arg Xaa Gly Cys Lys Xaa Cys
1               5                   10
```

```
<210> SEQ ID NO 15
<211> LENGTH: 10
<212> TYPE: PRT
<213> ORGANISM: Artificial Sequence
<220> FEATURE:
<223> OTHER INFORMATION: Pepetide 15 - Straight chain peptide starting
      material
<220> FEATURE:
<221> NAME/KEY: MISC_FEATURE
<222> LOCATION: (1)..(1)
<223> OTHER INFORMATION: homocysteine with Mmt protecting group
<220> FEATURE:
<221> NAME/KEY: MISC_FEATURE
<222> LOCATION: (2)..(2)
<223> OTHER INFORMATION: protected with tBu group
<220> FEATURE:
<221> NAME/KEY: MISC_FEATURE
<222> LOCATION: (3)..(3)
<223> OTHER INFORMATION: side chain amino group is substituted with iPr
      and Boc
<220> FEATURE:
<221> NAME/KEY: MISC_FEATURE
<222> LOCATION: (4)..(4)
<223> OTHER INFORMATION: (D)-isomer with Pbf protecting group
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (7)..(7)
<223> OTHER INFORMATION: Mmt protected
<220> FEATURE:
<221> NAME/KEY: MISC_FEATURE
<222> LOCATION: (8)..(8)
<223> OTHER INFORMATION: side chain amino group is substituted with iPr
      and Boc
<220> FEATURE:
<221> NAME/KEY: MISC_FEATURE
<222> LOCATION: (9)..(9)
<223> OTHER INFORMATION: PEG6 polymer liinker
<220> FEATURE:
<221> NAME/KEY: MISC_FEATURE
<222> LOCATION: (10)..(10)
<223> OTHER INFORMATION: Trt protected

<400> SEQUENCE: 15

Xaa Tyr Lys Arg Xaa Gly Cys Lys Xaa Cys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Compound F
<220> FEATURE:
<221> NAME/KEY: MISC_FEATURE
<222> LOCATION: (1)..(1)
<223> OTHER INFORMATION: homocysteine with acetylated alpha amino group
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of homocysteine and
      cysteine groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
```

```
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of cysteine
<220> FEATURE:
<221> NAME/KEY: MISC_FEATURE
<222> LOCATION: (10)..(10)
<223> OTHER INFORMATION: thiol functional group of cysteine attached to
      paclitaxel via -CH2-C(=O)- linker

<400> SEQUENCE: 16

Xaa Tyr Lys Arg Xaa Gly Cys Lys Xaa Cys
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Compound G - linked to eribulin
<220> FEATURE:
<221> NAME/KEY: MISC_FEATURE
<222> LOCATION: (1)..(1)
<223> OTHER INFORMATION: acetyl protected homocysteine
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (8)..(8)
<223> OTHER INFORMATION: terminal end of Lys is attached to eribulin via
      PEG6 linker and -CH2-C(=O)- linker

<400> SEQUENCE: 17

Xaa Tyr Lys Arg Xaa Gly Cys Lys
1               5

<210> SEQ ID NO 18
<211> LENGTH: 10
<212> TYPE: PRT
<213> ORGANISM: Artificial Sequence
<220> FEATURE:
<223> OTHER INFORMATION: Compound H with Paclitaxel
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
```

```
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of cysteine
<220> FEATURE:
<221> NAME/KEY: MISC_FEATURE
<222> LOCATION: (10)..(10)
<223> OTHER INFORMATION: thiol functional group of cysteine attached to
      paclitaxel via -CH2-C(=O)- linker

<400> SEQUENCE: 18

Xaa Tyr Lys Arg Xaa Gly Cys Lys Xaa Cys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Compound I - linked to paclitaxel
<220> FEATURE:
<221> NAME/KEY: MISC_FEATURE
<222> LOCATION: (1)..(1)
<223> OTHER INFORMATION: acetylated homocysteine
<220> FEATURE:
<221> NAME/KEY: MISC_FEATURE
<222> LOCATION: (1)..(7)
<223> OTHER INFORMATION: Forms cyclic structure via sulfur atoms and a
      linker -CH2-Phenyl-CH2-
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of cysteine
<220> FEATURE:
<221> NAME/KEY: MISC_FEATURE
<222> LOCATION: (10)..(10)
<223> OTHER INFORMATION: thiol functional group of cysteine attached to
      paclitaxel via -CH2-C(=O)- linker
```

-continued

```
<400> SEQUENCE: 19

Xaa Tyr Lys Arg Xaa Gly Cys Lys Xaa Cys
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Compound J - Linked to eribulin
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: Carboxyl end of Lys is linked to a PEG7
      polymeric linker with modified functional groups on both terminal
      ends to form an amide bond with Lys and the other end of PEG7 is
      linked to eribulin via an amide linkage.

<400> SEQUENCE: 20

Xaa Tyr Lys Arg Xaa Gly Cys Lys
1               5

<210> SEQ ID NO 21
<211> LENGTH: 8
<212> TYPE: PRT
<213> ORGANISM: Artificial Sequence
<220> FEATURE:
<223> OTHER INFORMATION: Compound K - CXCR4 Peptide linker
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
      and substituted with a PEG-6 linker with modified functional
``` groups on both terminal ends to form an amide bond with the
carboxy terminal of Lys and terminated -CH2-CH2-CO2H group on the
other end

<400> SEQUENCE: 21

Xaa Tyr Lys Arg Xaa Gly Cys Lys
1               5

<210> SEQ ID NO 22
<211> LENGTH: 10
<212> TYPE: PRT
<213> ORGANISM: Artificial Sequence
<220> FEATURE:
<223> OTHER INFORMATION: Compound L - CXCR4 linker terminated with Cys
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of cysteine

<400> SEQUENCE: 22

Xaa Tyr Lys Arg Xaa Gly Cys Lys Xaa Cys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Compound M
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE

```
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of lysine

<400> SEQUENCE: 23

Xaa Tyr Lys Arg Xaa Gly Cys Lys Xaa Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Compound N
<220> FEATURE:
<221> NAME/KEY: MISC_FEATURE
<222> LOCATION: (1)..(1)
<223> OTHER INFORMATION: acetylated homocysteine
<220> FEATURE:
<221> NAME/KEY: MISC_FEATURE
<222> LOCATION: (1)..(7)
<223> OTHER INFORMATION: cyclic structure is formed by formation of a
      di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
      on both terminal ends to form an amide bond with Lys and an amide
      bond with alpha-amino group of lysine
<220> FEATURE:
<221> NAME/KEY: MISC_FEATURE
<222> LOCATION: (10)..(10)
<223> OTHER INFORMATION: side chain amino group is substituted with
      azide

<400> SEQUENCE: 24

Xaa Tyr Lys Arg Xaa Gly Cys Lys Xaa Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Compound O - similar to Compound N with
      3-mercaptopropionic acid
<220> FEATURE:
<221> NAME/KEY: MISC_FEATURE
<222> LOCATION: (1)..(1)
<223> OTHER INFORMATION: 3-mercaptopropionic acid
<220> FEATURE:
<221> NAME/KEY: MISC_FEATURE
<222> LOCATION: (1)..(7)
<223> OTHER INFORMATION: cyclic structure is formed by formation of a
```

```
    di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
    on both terminal ends to form an amide bond with Lys and an amide
    bond with alpha-amino group of lysine
<220> FEATURE:
<221> NAME/KEY: MISC_FEATURE
<222> LOCATION: (10)..(10)
<223> OTHER INFORMATION: side chain amino group is substituted with
    azide

<400> SEQUENCE: 25

Xaa Tyr Lys Arg Xaa Gly Cys Lys Xaa Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Compound P
<220> FEATURE:
<221> NAME/KEY: MISC_FEATURE
<222> LOCATION: (1)..(1)
<223> OTHER INFORMATION: homocysteine with acetyl substituent on the
    alpha-amine group
<220> FEATURE:
<221> NAME/KEY: MISC_FEATURE
<222> LOCATION: (1)..(7)
<223> OTHER INFORMATION: cyclic structure is formed by formation of a
    di-sulfide linkage between sulfur atoms of two groups
<220> FEATURE:
<221> NAME/KEY: MISC_FEATURE
<222> LOCATION: (3)..(3)
<223> OTHER INFORMATION: side chain amino group is substituted with iPr
<220> FEATURE:
<221> NAME/KEY: MISC_FEATURE
<222> LOCATION: (4)..(4)
<223> OTHER INFORMATION: (D)-isomer
<220> FEATURE:
<221> NAME/KEY: MISC_FEATURE
<222> LOCATION: (5)..(5)
<223> OTHER INFORMATION: 2Nal
<220> FEATURE:
<221> NAME/KEY: MISC_FEATURE
<222> LOCATION: (8)..(8)
<223> OTHER INFORMATION: side chain amino group is substituted with iPr
<220> FEATURE:
<221> NAME/KEY: MISC_FEATURE
<222> LOCATION: (9)..(9)
<223> OTHER INFORMATION: a PEG-7 linker with modified functional groups
    on both terminal ends to form an amide bond with Lys and an amide
    bond with alpha-amino group of lysine

<400> SEQUENCE: 26

Xaa Tyr Lys Arg Xaa Gly Cys Lys Xaa Lys
1               5                   10
```

What is claimed is:

1. A selective CXCR4 binding peptide conjugate ("PC") of the formula:

(SEQ ID NO: 3)

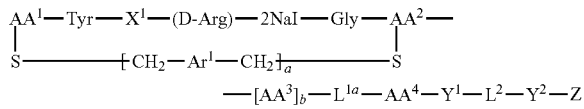

or a pharmaceutically acceptable salt thereof,
wherein:
- a is 0 or 1;
- b is 1;
- $AA^1$ along with the sulfur atom that is attached thereto is 3-mercaptopropionic acid, optionally substituted cysteine, optionally substituted homocysteine, or optionally substituted penicillamine;
- $AA^2$ along with the sulfur atom that is attached thereto is cysteine or homocysteine;
- $Ar^1$ is phenylene;
- $X^1$ is Arg, Dap, Dab, Orn, Lys, Dap(iPr), Dab(iPr), Orn(iPr), or Lys(iPr);
- $AA^3$ is Lys(iPr);
- $AA^4$ is an amino acid or a derivative thereof;
- $Y^1$ is a side-chain function group of amino acid $AA^4$;
- $L^{1a}$ is a polyethylene glycol of about 2 to about 20 monomers;
- $L^2$ is a non-polymeric linker;
- Z a medically useful compound; and
- $Y^2$ is a functional group of said medically useful compound or a functional group of $L^2$;

and wherein one or more of $AA^1$, $AA^2$, $X^1$, $AA^3$, and $AA^4$ are optionally isotopically labelled.

2. The selective CXCR4 binding peptide conjugate according to claim 1, wherein $L^{1a}$ is a polyethylene glycol of about 2 to about 10 monomers.

3. The selective CXCR4 binding peptide conjugate according to claim 1, wherein Z is an anticancer agent.

4. The selective CXCR4 binding peptide conjugate according to claim 3, wherein said anticancer agent is selected from the group consisting of paclitaxel, Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbestrol, Eribulin, Ethinyl, estradiol, Etoposide, Mitomycin, Mitotane, Mitoxantrone, Pentastatin, Pipobroman, Plicamycin, Prednisone, Procarbazine, Streptozocin, Tamoxifen, Teniposide, Vinblastine, and Vincristine.

5. The selective CXCR4 binding peptide conjugate according to claim 1, wherein $AA^1$ along with the sulfur atom that is attached thereto is optionally substituted cysteine.

6. The selective CXCR4 binding peptide conjugate according to claim 5, wherein α-amino group of $AA^1$ is substituted with an acetyl group.

7. The selective CXCR4 binding peptide conjugate according to claim 1, wherein $AA^2$ along with the sulfur atom that is attached thereto is optionally substituted cysteine.

8. The selective CXCR4 binding peptide conjugate according to claim 1, wherein $X^1$ is Lys(iPr) or Lys(deuterated-iPr).

9. The selective CXCR4 binding peptide conjugate according to claim 1, wherein $Ar^1$ is phenyl.

10. A method for treating a subject suffering from a cancer, said method comprising administering to the subject a therapeutically effective amount of a selective CXCR4 binding peptide conjugate of claim 1, wherein said medically useful compound is an anticancer agent.

11. The method of claim 10, wherein said cancer is selected from the group consisting of breast cancer, lung cancer, pancreatic cancer, kidney cancer, brain cancer, blood cancer, leukemia, prostate cancer, ovarian cancer, and bladder cancer.

* * * * *